US009456798B2

(12) United States Patent
Xue et al.

(10) Patent No.: US 9,456,798 B2
(45) Date of Patent: Oct. 4, 2016

(54) METHODS AND APPARATUS FOR INDIVIDUALLY OPTIMIZING UNIFORM CONTRAST ENHANCEMENTS IN COMPUTED TOMOGRAPHY IMAGING

(71) Applicants: Ming Xue, Ellicott City, MD (US); Wei Lu, Ellicott City, MD (US); Seth Kligerman, Baltimore, MD (US); Hao Zhang, Potomac, MD (US); Warren D'Souza, Timonium, MD (US); Wookjin Choi, Baltimore, MD (US)

(72) Inventors: Ming Xue, Ellicott City, MD (US); Wei Lu, Ellicott City, MD (US); Seth Kligerman, Baltimore, MD (US); Hao Zhang, Potomac, MD (US); Warren D'Souza, Timonium, MD (US); Wookjin Choi, Baltimore, MD (US)

(73) Assignee: The University of Maryland, Baltimore, Baltimore, MD (US)

( * ) Notice: Subject to any disclaimer, the term of this patent is extended or adjusted under 35 U.S.C. 154(b) by 0 days.

(21) Appl. No.: 14/710,052

(22) Filed: May 12, 2015

(65) Prior Publication Data

US 2015/0324979 A1 Nov. 12, 2015

Related U.S. Application Data

(60) Provisional application No. 61/991,659, filed on May 12, 2014.

(51) Int. Cl.
*G06K 9/00* (2006.01)
*A61B 6/00* (2006.01)
(Continued)

(52) U.S. Cl.
CPC .............. *A61B 6/545* (2013.01); *A61B 6/032* (2013.01); *A61B 6/481* (2013.01); *A61B 6/486* (2013.01);
(Continued)

(58) Field of Classification Search
CPC ...... A61B 6/032; A61B 6/481; A61B 6/486; A61B 6/504; A61B 6/545; G06T 11/006; G06T 7/0012; G06T 7/0081; G06T 2207/10081; G06T 2207/20104; G06T 2207/30101; G06T 2211/404
See application file for complete search history.

(56) References Cited

U.S. PATENT DOCUMENTS

2005/0251010 A1* 11/2005 Mistretta ................ A61B 6/025
  600/407
2010/0030073 A1*  2/2010 Kalafut .................. A61B 6/481
  600/431

(Continued)

OTHER PUBLICATIONS

Xue et al ("Individually optimized uniform contrast enhancement in CT angiography for the diagnosis of pulmonary thromboembolic disease—A simulation study", Med. Phys. 40(2), Dec. 2013).*

(Continued)

*Primary Examiner* — Amara Abdi
(74) *Attorney, Agent, or Firm* — Eugene J. Molinelli; Buesse Wolter Sanks & Maire

(57) ABSTRACT

A method is provided for optimizing a contrast injection function for CT imaging. The method includes injecting, with an injector pump, a test bolus of a contrast agent into a subject. The method also includes computing, on a processor, an impulse enhancement function. The method also includes determining, on a processor, a target enhancement function for a region of interest. The method also includes determining, with a processor, a plurality of parameters for a functional form for a contrast injection function in a time domain. The method also includes determining for the contrast injection function a constraint. The method also includes determining, with a processor, particular values for the plurality of parameters, which satisfy the constraint and minimize a difference between a value of an enhancement function and the target enhancement function computed in the time domain at discrete time periods without use of a Fourier transform.

29 Claims, 9 Drawing Sheets

(51) Int. Cl.
G06T 7/00 (2006.01)
G06T 11/00 (2006.01)
A61B 6/03 (2006.01)
(52) U.S. Cl.
CPC .............. A61B 6/504 (2013.01); G06T 7/0012 (2013.01); G06T 7/0081 (2013.01); G06T 11/006 (2013.01); G06T 2207/10081 (2013.01); G06T 2207/20104 (2013.01); G06T 2207/30101 (2013.01); G06T 2211/404 (2013.01)

(56) References Cited

U.S. PATENT DOCUMENTS

| | | | | |
|---|---|---|---|---|
| 2010/0204572 | A1* | 8/2010 | Kalafut | A61B 6/507 600/431 |
| 2013/0211247 | A1* | 8/2013 | Kalafut | A61B 6/507 600/432 |
| 2013/0324845 | A1* | 12/2013 | Korporaal | A61B 6/481 600/431 |

OTHER PUBLICATIONS

Fleischmann et al. ("mathematical analysis of arterial enhancement and optimization of Bolos geometry for CT Angiography using the discrete Fourier transform", Journal of computer assisted tomography, Jun. 1999, pp. 474-484).*
Bae, K., et al., "Multiphasic Injection Method for Uniform Prolonged Vascular Enhancement at CT Angiography: Pharmacokinetic Analysis and Experimental Porcine Model," Radiology, 2000, pp. 872-880, vol. 216.
Bae, K., et al., "Uniform Vascular Contrast Enhancement and Reduced Contrast Medium Volume Achieved by Using Exponentially Decelerated Contrast Material Injection Method," Radiology, 2004, pp. 732-736, vol. 231, No. 3.
Bae, K., et al., "Effect of Patient Weight and Scanning Duration on Contrast Enhancement during Pulmonary Multidetector CT Angiography," Radiology, 2007, pp. 582-589, vol. 242, No. 2.
Bae, K., "Optimization of Contrast Enhancement in Thoracic MDCT," Radiologic Clinics of North America, 2010, pp. 9-29, vol. 48, No. 1, Publisher: Elsevier Inc.
Bae, K., "Intravenous Contrast Medium Administration and Scan Timing at CT: Considerations and Approaches," Radiology, Jul. 2010, pp. 32-61, vol. 256, No. 1.
Baile, E., et al., "Spiral Computed Tomography Is Comparable to Angiography for the Diagnosis of Pulmonary Embolism," Am J Respir Crit Care Med, 2000, pp. 1010-1015, vol. 161.
Cao, L., et al., "Multiphase contrast-saline mixture injection with dual-flow in 64-row MDCT coronary CTA," European Journal of Radiology, 2009, pp. 496-499, vol. 69, Publisher: Elsevier Ireland Ltd.
Driscoll, B., et al., "Development of a dynamic flow imaging phantom for dynamic contrast-enhanced CT," Med. Phys., 2011, pp. 4866-4880, vol. 38, No. 8.
Fleischmann, D., et al., "Quantification of Intravenously Administered Contrast Medium Transit through the Peripheral Arteries: Implications for CT Angiography," Radiology, 2005, pp. 1076-1082, vol. 236.
Fleischmann, D., et al., "Mathematical Analysis of Arterial Enhancement and Optimization of Bolus Geometry for CT Angiography Using the Discrete Fourier Transform," Journal of Computer Assisted Tomography, May/Jun. 1999, pp. 474-484, vol. 23, No. 3, Publisher: Lippincott Williams & Wilkins, Inc.
Fleischmann, D., et al., "Improved Uniformity of Aortic Enhancement with Customized Contrast Medium Injection Protocols at CT Angiography," Radiology, 2000, vol. 214, No. 363-371.
Fleischmann, D., "Use of high concentration contrast media: principles and rationale-vascular district," European Journal of Radiology, 2003, pp. S88-S93, vol. 45, No. Suppl. 1, Publisher: Elsevier Science Ireland Ltd.
Fleischmann, D., "How to design injection protocols for multiple detector-row CT angiography (MDCTA)," Eur. Radiol. Suppl., 2005, pp. E60-E65, vol. 15, No. Suppl. 5, Publisher: Springer-Verlag.
Fleischmann, D., "CT Angiography: Injection and Acquisition Technique," Radio. Clin. N. Am., 2010, pp. 237-247, vol. 48.
Goldhaber, S., et al., "Pulmonary embolism and deep vein thrombosis," Lancet, May 12, 2012, pp. 1835-1846, vol. 379.
Hanninen, E., et al., "Detection of Focal Liver Lesions at Biphasic Spiral CT: Randomized Double-Blind Study of the Effect of Iodine Concentration in Contrast Materials," Radiology, 2000, pp. 403-409, vol. 216.
Hawley, P., et al., "Difficulties in diagnosing pulmonary embolism in the obese patient: A literature review," Vascular Medicine, 2011, pp. 1-8.
Hittmair, K., et al., "Accuracy of Predicting and Controlling Time-Dependent Aortic Enhancement from a Test Bolus Injection," Journal of Computer Assisted Tomography, 2001, pp. 287-294, vol. 25, No. 2, Publisher: Lippincott Williams & Wilkins, Inc., Published in: Philadelphia, USA.
Jones, S., et al., "The Indeterminate CT Pulmonary Angiogram: Imaging Characteristics and Patient Clinical Outcome," Radiology, 2005, pp. 329-337, vol. 237.
Kerl, J., et al., "Right Heart: Split-Bolus Injection of Diluted Contrast Medium for Visualization at Coronary CT," Radiology, 2008, pp. 356-364, vol. 247, No. 2.
Kim, S., et al., "A method for patient dose reduction in dynamic contrast enhanced CT study," Med. Phys., Sep. 2011, pp. 5094-5103, vol. 38, No. 9.
Kim, S., et al., "Multiphasic contrast injection for improved precision of parameter estimates in functional CT," Med. Phys., Dec. 2008, pp. 5921-5933, vol. 35, No. 12.
Kim, S., et al., "Interindividual variability of arterial impulse response to intravenous injection of nonionic contrast agent (Iohexol) in DCE-CT study," Med. Phys., Oct. 2009, pp. 4791-4802, vol. 36, No. 10.
Kligerman, S., et al., "Use of a Hybrid Iterative Reconstruction Technique to Reduce Image Noise and Improve Image Quality in Obese Patients Undergoing Computed Tomographic Pulmonary Angiography," J. Thorac. Imaging, Jan. 2013, pp. 49-59, vol. 28, No. 1.
Lee, C., et al., "Determination of Optimal Timing Window for Pulmonary Artery MDCT Angiography," Am. J. Roentgenol, Feb. 2007, pp. 313-317, vol. 188.
Marin, D., et al., "Low-Tube-Voltage, High-Tube-Current Multidetector Abdominal CT: Improved Image Quality and Decreased Radiation Dose with Adaptive Statistical Iterative Reconstruction Algorithm-Initial Clinical Experience," Radiology, Jan. 2010, pp. 145-153, vol. 254, No. 1.
Numburi, U., et al., "Patient-specific Contrast Injection Protocols for Cardiovascular Multi-detector Row Computed Tomography," Journal of Computer Assisted Tomography, Mar./Apr. 2007, pp. 281-289, vol. 31, No. 2, Publisher: Lippincott Williams & Wilkins.
Patel, S., et al., "Pulmonary Embolism: Optimization of Small Pulmonary Artery Visualization at Multi-Detector Row CT," Radiology, 2003, pp. 455-460, vol. 227.
Riordan, A., et al., "Validation of CT brain perfusion methods using a realistic dynamic head phantom," Medical Physics, 2011, pp. 3212-3221, vol. 38, Publisher: American Association of Physicists in Medicine.
Roggenland, D., et al., "CT Angiography in Suspected Pulmonary Embolism: Impact of Patient Characteristics and Different Venous Lines on Vessel Enhancement and Image Quality," Am. J. Rotengenol, Jun. 2008, pp. W351-W359, vol. 190.
Sagel, S., et al., "Nonuniform Pulmonary Arterial Perfusion: Pulmonary Embolism?," Radiology, 1970, pp. 541-548, vol. 99.
Schoepf, U., et al., "CT Angiography for Diagnosis of Pulmonary Embolism: State of the Art," Radiology, 2004, pp. 329-337, vol. 230.
Schramm, P., et al., "How does the injection protocol influence the attenuation-time curve in CT perfusion measurements: Comparison of measured and simulated data," Med. Phys., Aug. 2009, pp. 3487-3494, vol. 36, No. 8.

(56) References Cited

OTHER PUBLICATIONS

Skrok, J., et al., "Pulmonary Arterial Hypertension: MR Imaging-derived First-Pass Bolus Kinetic Parameters Are Biomarkers for Pulmonary Hemodynamics, Cardiac Function, and Ventricular Remodeling," Radiology, Jun. 2012, pp. 678-687, vol. 263, No. 3.
Sostman, H., et al., "Acute Pulmonary Embolism: Sensitivity and Specificity of Ventilation-Perfusion Scintigraphy in PIOPED II Study," Radiology, Mar. 2008, pp. 941-946, vol. 246, No. 3.
Utsunomiya, D., et al., "Cardiac 16-MDCT for Anatomic and Functional Analysis: Assessment of a Biphasic Contrast Injection Protocol," Am. J. Roentgenol, 2006, pp. 638-644, vol. 187.
Weininger, M., et al., "Cardiothoracic CT Angiography: Current Contrast Medium Delivery Strategies," Am. J. Roentgeol, Mar. 2011, pp. W260-W272, vol. 196.
Wittram, C., et al., "Acute and Chronic Pulmonary Emboli: Angiography-CT Correlation," Am. J. Roentgenol, Jun. 2006, pp. S421-S429, vol. 186.
Xue, M., et al., "Individually optimized uniform contrast enhancement in CT angiography for the diagnosis of pulmonary thromboembolic disease—A simulation study," Dec. 2013, pp. 121906-1-121906-9, vol. 40, No. 12.

* cited by examiner

METHODS AND APPARATUS FOR INDIVIDUALLY OPTIMIZING UNIFORM CONTRAST ENHANCEMENTS IN COMPUTED TOMOGRAPHY IMAGING

CROSS-REFERENCE TO RELATED APPLICATIONS

This application claims benefit of Provisional Appln. 61/991,659, filed May 12, 2014, the entire contents of which are hereby incorporated by reference as if fully set forth herein, under 35 U.S.C. §119(e).

BACKGROUND

Computed Tomography Pulmonary Angiography (CTPA) are medical diagnostic tests that use computed tomography (CT) to obtain an image of the pulmonary arteries, for purposes of diagnosing pulmonary thromboembolic disease (PE). Prior to undergoing a CTPA, contrast agent is injected into the subject, based on a contrast injection function, to produce a desired enhancement pattern of a region of interest (ROI) within the pulmonary arteries. Bolus shaping is a technique of determining the contrast injection function, in order to produce the desired enhancement pattern. Various conventional methods of bolus shaping are known, including an exponentially decelerated injection (EDI) function derived from a complex compartment model and a bi-phasic or multi-phasic injection using a discrete Fourier transform (DFT) approach.

SUMMARY

The conventional methods for bolus shaping are deficient since they are not individually optimized for each subject and cannot be practically implemented on current injector pumps. With the EDI approach, inter-subject variation of contrast enhancement is not taken into consideration, and a fixed injection function $4e^{-0.01\tau}$ (in units of milliliters per second or ml/second) is used for all subjects. In addition, most current injector pumps cannot produce exponentially decelerated rates of injection. In the DFT approach, a Fourier transform is used to compute contrast injection functions that are continuously changing and may involve unrealistic negative flow rates, which also cannot be implemented on current injector pumps.

In a first set of embodiments, a method is provided for optimizing a contrast injection function. The method includes injecting, with an injector pump, a test bolus of a contrast agent into a subject and scanning, with a scanner, a region of interest to obtain a test enhancement function. The method further includes computing, on a processor, an impulse enhancement function based on the test enhancement function. The method further includes determining, based on the contrast agent, a target enhancement function for the region of interest. The method further includes determining, on the processor, a plurality of parameters for a functional form for the contrast injection function in a time domain. The method further includes determining, for the contrast injection function, a constraint comprising at least a total volume of contrast agent. The method further includes determining, on the processor, an enhancement function based on the impulse enhancement function and the contrast injection function. The method further includes determining, on the processor, particular values for the plurality of parameters, which satisfy the constraint and minimize a difference between a value of the enhancement function and the target enhancement function, where the difference is computed in the time domain at discrete time periods without use of a Fourier transform. The method further includes injecting, with the injector pump, the contrast agent into the subject based on the contrast injection function using the particular values for the plurality of parameters.

In some embodiments of the first set, the functional form for the contrast injection function is multiphasic to conform to controls for the injector pump.

In some embodiments of the first set, the difference between the enhancement function and the target enhancement function is minimized using a mixed integer solution, where at least one parameter is based on an integer variable.

In some embodiments of the first set, the parameter based on the integer variable is a time for a change in a rate of injection at each discrete time period, where the integer variable is a binary integer variable selected from the domain $\{0, 1\}$, and the constraint is a sum of the times for changes in the rate of injection. In some embodiments of the first set, the parameter based on the integer variable is a switch for a rate of injection at each discrete time period, the integer variable is a binary integer variable selected from the domain $\{0, 1\}$ and the value of the rate of injection at each discrete time period is given by a product of the switch parameter and a value within a range between a minimum value and a maximum value.

In a second set of embodiments, an apparatus is provided for optimizing a contrast injection function. The apparatus includes an injector pump to deliver contrast agent to a subject. The apparatus further includes a processor to transmit a contrast injection function to the injector pump to cause the injector pump to deliver the contrast agent based on the contrast injection function. The processor is configured to determine the contrast injection function such that a difference between an enhancement function of the contrast injection function and a target enhancement function is minimized over a time domain at discrete time periods without determining a Fourier transform.

In some embodiments of the second set, the apparatus includes a scanner to detect images of a region of interest of the subject after delivery of the contrast agent and the processor is configured to determine the enhancement function based on image data received from the scanner.

Still other aspects, features, and advantages of the invention are readily apparent from the following detailed description, simply by illustrating a number of particular embodiments and implementations, including the best mode contemplated for carrying out the invention. The invention is also capable of other and different embodiments, and its several details can be modified in various obvious respects, all without departing from the spirit and scope of the invention. Accordingly, the drawings and description are to be regarded as illustrative in nature, and not as restrictive.

DETAILED DESCRIPTION

Figure 1:
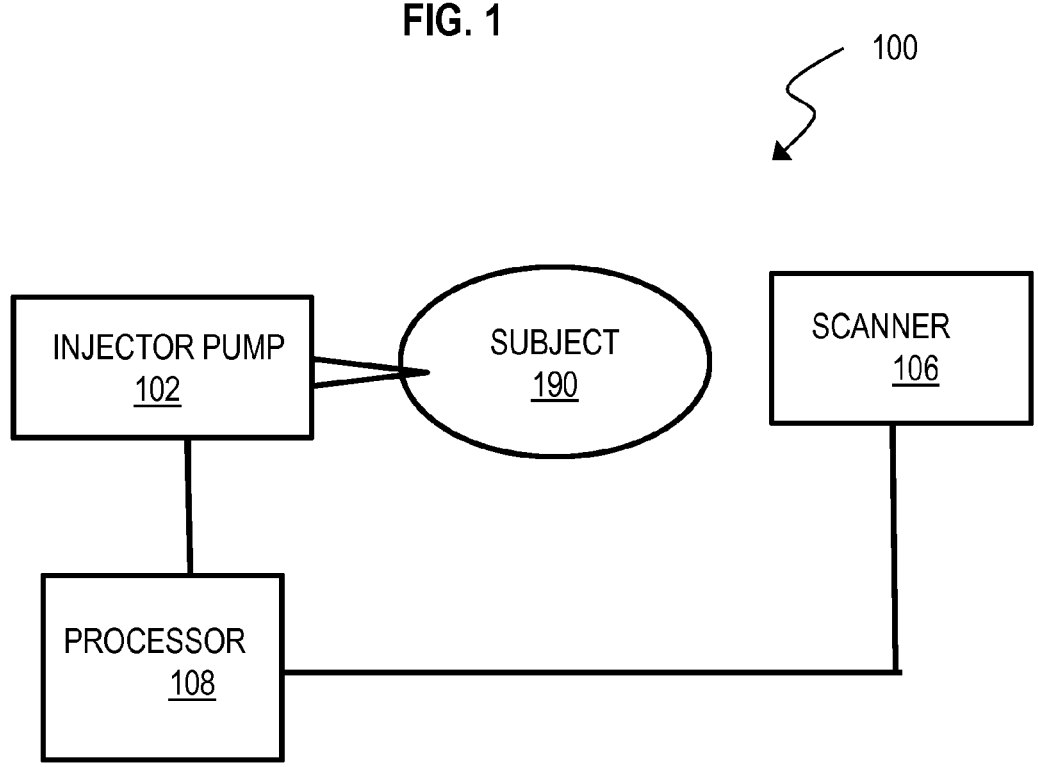
FIG. 1 is a block diagram that illustrates an example of an apparatus for optimizing a contrast injection function, according to one embodiment.

A method and apparatus are described for individually optimizing a contrast injection function for contrast enhanced computed tomography (CT). For purposes of the following description, a contrast injection function is defined as a time-dependent rate of injection (e.g., in units of milliliters per second or ml/sec) of a contrast agent that is delivered from an injector pump into a subject. After the contrast agent is injected into the subject based on the contrast injection function, CT (computed tomography) images of a region of interest (ROI) within a target organ of the subject are captured, and an enhancement function is determined. For purposes of the following description, the enhancement function is defined as a measure of radiodensity (in units of Hounsfield or HU) of the captured images in the time domain. The HU unit is on a scale in which air has a radiodensity of 1000 HU and water has a radiodensity of 0 HU.

In the following description, for the purposes of explanation, numerous specific details are set forth in order to provide a thorough understanding of the present invention. It will be apparent, however, to one skilled in the art that the present invention may be practiced without these specific details. In other instances, well-known structures and devices are shown in block diagram form in order to avoid unnecessarily obscuring the present invention.

Notwithstanding that the numerical ranges and parameters setting forth the broad scope are approximations, the numerical values set forth in specific non-limiting examples are reported as precisely as possible. Any numerical value, however, inherently contains certain errors necessarily resulting from the standard deviation found in their respective testing measurements. Unless otherwise clear from the context, a numerical value presented herein has an implied precision given by the least significant digit. Thus a value 1.1 implies a value from 1.05 to 1.15. The term "about" is used to indicate a broader range centered on the given value, and unless otherwise clear from the context implies a broader rang around the least significant digit, such as "about 1.1" implies a range from 1.0 to 1.2. If the least significant digit is unclear, then the term "about" implies a factor of two, e.g., "about X" implies a value in the range from 0.5X to 2X, for example, about 100 implies a value in a range from 50 to 200. Moreover, all ranges disclosed herein are to be understood to encompass any and all sub-ranges subsumed therein. For example, a range of "less than 10" can include any and all sub-ranges between (and including) the minimum value of zero and the maximum value of 10, that is, any and all sub-ranges having a minimum value of equal to or greater than zero and a maximum value of equal to or less than 10, e.g., 1 to 4.

Some embodiments of the invention are described below in the context of a method and system for optimizing a contrast injection function for each individual undergoing a CT angiography for pulmonary thromboembolic disease. However, the invention is not limited to this context. In other embodiments, the embodiments of the invention may be used to optimize a contrast injection function, such as a wide range of contrast enhanced computed tomography procedures including perfusion CT, pulmonary CT angiography, aortic/coronary CT angiography, peripheral CT angiography, contrast enhanced abdominal CT, and contrast enhanced 4D-CT simulation, among others.

1. OVERVIEW

Pulmonary thromboembolic disease (PE) is the third most common cause of cardiovascular related death after myocardial infarction and stroke. With the advent of multidetector computerized tomography (MDCT), CT has largely replaced ventilation-perfusion scanning as the most commonly ordered study to evaluate for PE. However, in order for a CT pulmonary angiography (CTPA) to be diagnostic, uniform contrast enhancement of the pulmonary arterial tree is desirable. Various factors are involved in obtaining uniform contrast enhancement for CTPA including cardiac output and body habitus; venous access factors including size and location of the intravenous (IV) injection; contrast delivery factors including injection rate, total contrast volume and injection protocol (i.e. uniphasic versus biphasic);

and scanner related factors including delay between the start of the scan and contrast administration.

With the continued evolution of MDCT, the acquisition of the entire pulmonary arterial tree with submillimeter spatial resolution can be attained in only a few seconds. In order to accommodate these faster scan times, the contrast injection function of the contrast agent can be adjusted, to provide properly timed peak enhancement of the pulmonary arteries during CTPA. Bolus shaping is a technique that designs the contrast injection function of the contrast agent, to produce the desired enhancement function for the target organ. The bolus shaping technique develops an optimized contrast injection function that can produce more uniform or plateau-like enhancement functions and makes the prediction of the optimal scan timing less difficult and more forgiving.

FIG. 1 is a block diagram that illustrates an example of an apparatus 100 for optimizing a contrast injection function, according to one embodiment. As illustrated in FIG. 1, the apparatus 100 includes an injector pump 102 to deliver contrast agent to a subject 190. The apparatus 100 also includes a processor 108 to transmit a contrast injection function to the injector pump 102 to cause the injector pump to deliver the contrast agent based on the contrast injection function. The apparatus 100 also includes a scanner 106 to capture CT images of the region of interest (ROI) of the subject, after injection of the contrast agent. The processor 108 determines the enhancement function based on image data of the CT images received from the scanner 106. Although a subject 190 is depicted for purposes of illustration the subject is not part of the apparatus 100. A subject is any human or animal used for test or evaluation or clinical diagnosis or treatment or any surrogate for same.

Prior to the injection of the contrast agent with the injector pump 102, the processor 108 initially determines the contrast injection function such that a difference between the enhancement function of the contrast injection function and a target enhancement function is minimized over a time domain at discrete time periods without determining a Fourier transform. In some embodiments, the processor 108 is a computer system as described below with reference to FIG. 9 or a chip set described below with reference to FIG. 10. The hardware used to form the processor 108 of the apparatus 100 is described in more detail below in the Computational Hardware Overview section.

Figure 2:
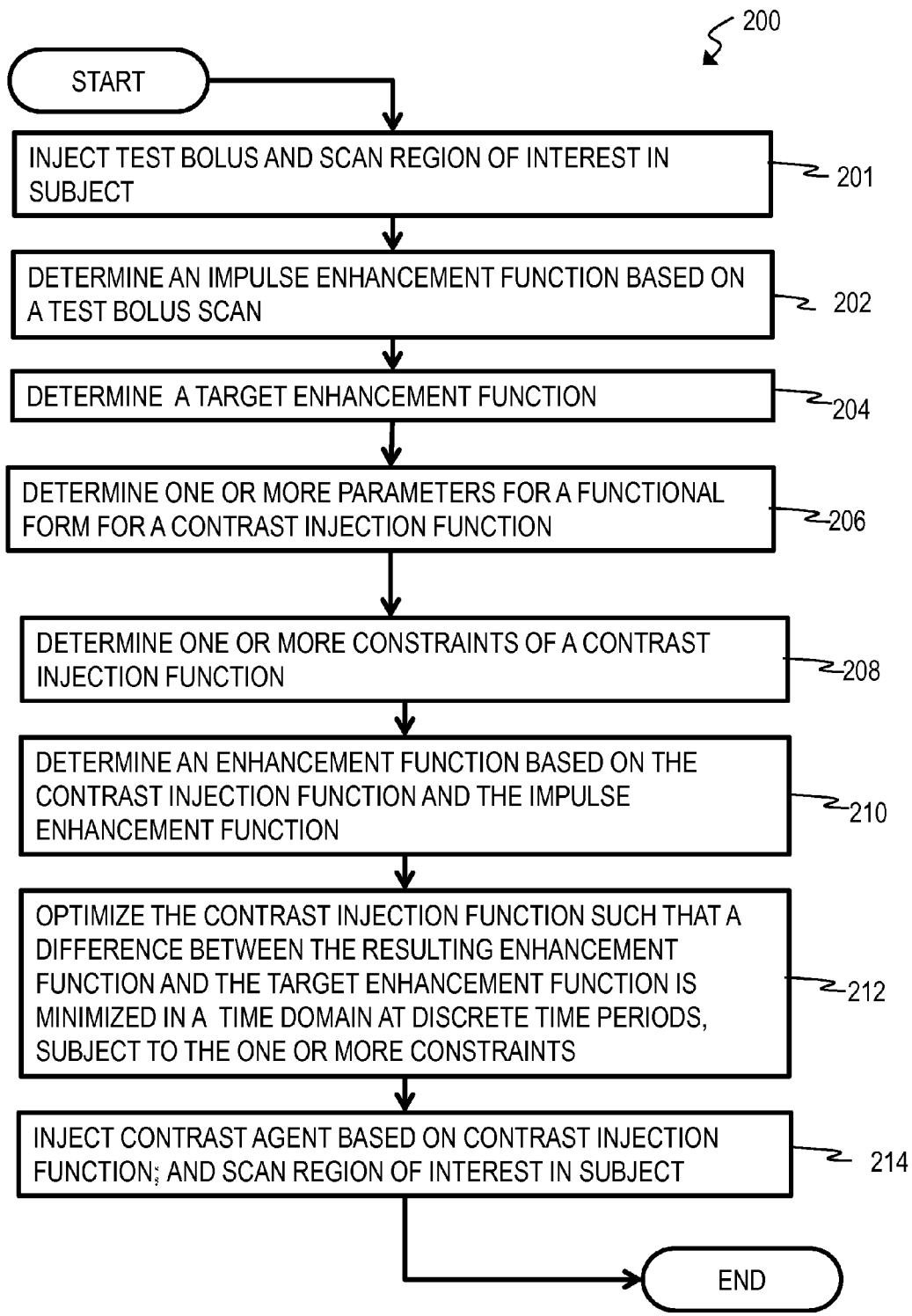
FIG. 2 is a flow diagram that illustrates an example of a method for optimizing a contrast injection function, according to one embodiment.

FIG. 2 is a flow diagram that illustrates an example of a method 200 for optimizing a contrast injection function, according to one embodiment. Although the flow diagram of FIG. 2 is depicted as integral steps in a particular order for purposes of illustration, in other embodiments one or more steps, or portions thereof, are performed in a different order, or overlapping in time, in series or in parallel, or are deleted, or one or more other steps are added, or the method is changed in some combination of ways.

Figure 3:
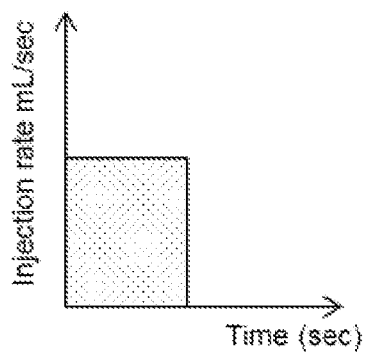
FIG. 3 illustrates an example of a test injection function, according to one embodiment.

After starting, in block 201, a test bolus of a contrast agent is injected, with the injector pump 102, into the subject 190, based on a test injection function. FIG. 3 illustrates an example of a test injection function, according to one embodiment, where the vertical axis is the rate of injection (in units of milliliters per second or ml/sec) and the horizontal axis is time (in units of seconds or sec). As depicted in FIG. 3, the test injection function has a fixed rate of injection for the test bolus of the contrast agent over a specific time period. In an example embodiment, the test bolus of the contrast agent is injected intravenously into the patient. In some embodiments, the total contrast agent injected for the test bolus is a small fraction of a total allowed volume of contrast agent for a patient during the procedure. The total allowed volume is determined based on the patient size and weight and the contrast agent used, as is well known in the art. Any contrast agents known at the time may be used, such as non-ionic contrast agents including Iopamidol, Iohexol, Ioxilan, Iopromide and Iodixanol and iconic contrast agents including Diatrizoate, Metrizoate and Ioxaglate.

Figure 5A:
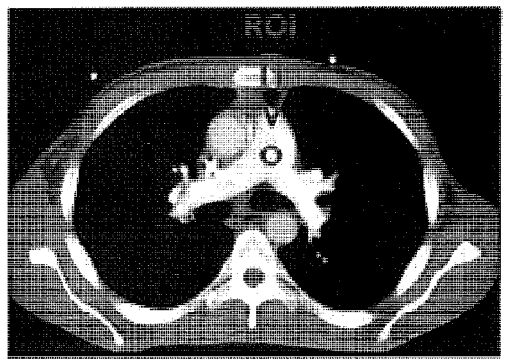
FIG. 5A illustrates an example of a CT image of a pulmonary artery, according to one embodiment.
Figure 5B:
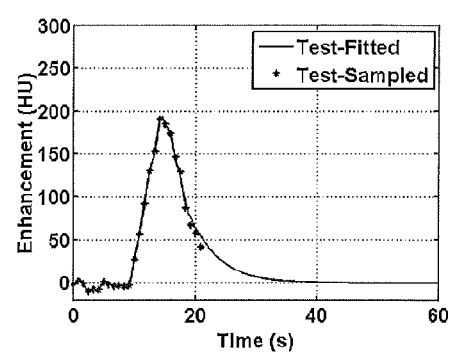
FIG. 5B illustrates an example of a test enhancement function based on the test injection function of FIG. 3, according to one embodiment.

Additionally, in block 201, a region of interest (ROI) of the subject 190 is scanned with the scanner 106 to obtain a test bolus scan, also called a test enhancement function. The ROI is determined, based on the specific procedure being conducted. FIG. 5B illustrates an example of a test enhancement function based on the test injection function of FIG. 3, according to one embodiment, where the vertical axis is the measured radiodensity (in units of Hounsfield or HU) of the scanned images and the horizontal axis is time (in units of seconds or sec).

Figure 5C:
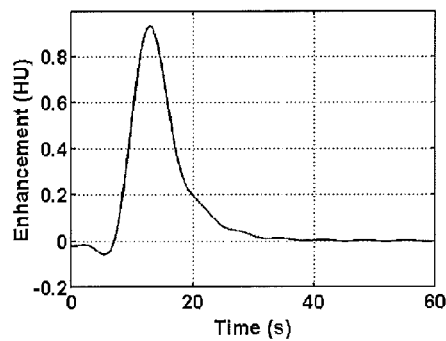
FIG. 5C illustrates an example of an impulse enhancement function, according to one embodiment.

In block 202, an impulse enhancement function is determined by the processor 108, based on the test bolus scan. The processor 108 determines the impulse enhancement function, by initially performing a Fourier transform of the test enhancement function and performing a Fourier transform of the test injection function to obtain these functions in the frequency domain (inverse time domain). The processor 108 then determines a ratio of the Fourier transform of the test enhancement function to the Fourier transform of the test injection function at each frequency, and subsequently performs an inverse Fourier transform of this ratio to obtain the impulse enhancement function in the time domain. Thus, the impulse enhancement function h(t) can be expressed according to Equation 1.

$$h(t) = FT^{-1}\left[\frac{FT(e_T(t))}{FT(i_T(t))}\right] \quad (1)$$

Where $i_T(t)$ is the test injection; $e_T(t)$ is the test enhancement function; FT denotes a Fourier transform operator and $FT^{-1}$ denotes an inverse Fourier transform operator. FIG. 5C illustrates an example of an impulse enhancement function, according to one embodiment, where the vertical axis is a measure of radiodensity (in units of Hounsfield or HU) based on a unit rate of injection and the horizontal axis is time (in units of seconds or sec). The impulse enhancement function models an individual subject's response to an injection function and is independent of the test injection function applied to the subject in block 201.

Figure 5D:
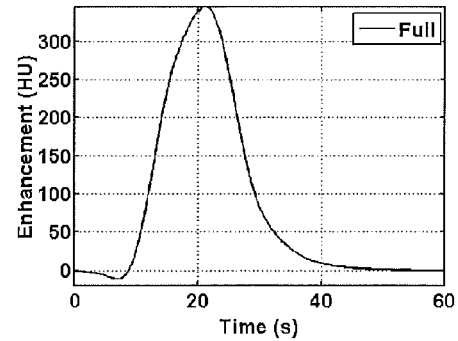
FIG. 5D illustrates an example of a simulated enhancement function, according to one embodiment.
Figure 5E:
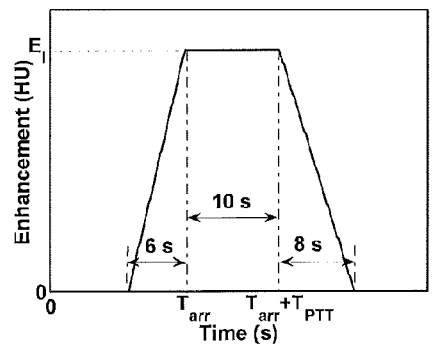
FIG. 5E illustrates an example of a target enhancement function, according to one embodiment.

In block 204, a target enhancement function is determined for the region of interest. FIG. 5E illustrates an example of a target enhancement function, according to one embodiment, where the vertical axis is the measured radiodensity (in units of Hounsfield or HU) averaged over the region of interest and the horizontal axis is time (in seconds or sec). As illustrated in FIG. 5E, the target enhancement function includes a rising region for a first time period, a plateau region for a second time period and a falling region for a third time period. In some embodiments a desired plateau and duration for the plateau is selected arbitrarily. The time of the plateau is determined however based on the test bolus scan, as described in more detail below.

Figure 8A:
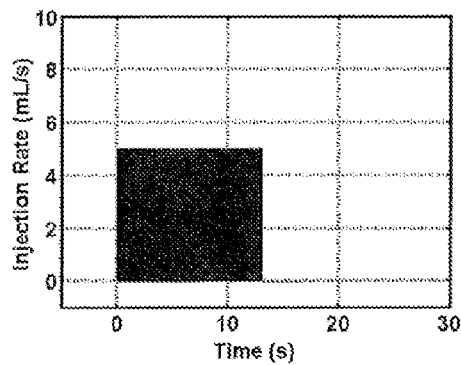
FIG. 8A illustrates an example of a simulated injection function, according to one embodiment.

In some embodiments, the plateau level is also based on the impulse response from the test bolus to ensure that the selected target is realistic and achievable for the particular subject. To determine a plateau value $E_1$ of the target enhancement function at the plateau region, a simulated full bolus of the contrast agent is first injected, with the injector pump 102, into the subject 190 based on a simulated injected function. FIG. 8A illustrates an example of a simulated injection function, according to one embodiment. In an example, the simulated injection function has a longer time duration and a larger total contrast volume than the test injection function depicted in FIG. 3. Based on the simulated injection function, a scan of the region of interest of the subject 190 is simulated to obtain a simulated enhancement function. FIG. 5D illustrates an example of a simulated enhancement function based on the simulated injection function, according to one embodiment, where the vertical axis is the measured radiodensity (in HU) of the scanned images and the horizontal axis is time (in units of seconds or sec). In this illustrated embodiment, the processor 108 determines the plateau value $E_1$ of the target enhancement function, based on a maximum value maintained by the simulated enhancement function over a minimum time period.

In an example embodiment, the minimum time period is in a range between 8-10 seconds. In another example, the processor 108 can determine the plateau level $E_1$ of the target enhancement function, based on a maximum level of the test enhancement function obtained in block 201. In an example embodiment, the plateau level $E_1$ of the target enhancement function is 300 HU.

The timing of the plateau is also based on the test bolus scan. As depicted in the example target enhancement function, an initial time $T_{arr}$ is a time delay between the contrast agent being injected into the subject and a peak amount of the contrast agent arriving at the region of interest. The initial time $T_{arr}$ is determined, based on an initial time period of the test enhancement function of FIG. 5B when an average value of the enhancement function is less than a threshold value indicating that a peak amount of the contrast agent has not arrived at the region of interest. The time period of the plateau region is determined, based on a transmit time of the contrast agent through the region of interest. In an example embodiment, the time period of the plateau region is adjusted to be greater than the actual transmit time of the contrast agent through the region of interest, to ensure that the contrast agent is within the region of interest during the time period of the plateau region. In an example embodiment, the time period of the plateau region is in a range of 10-12 seconds and the actual transmit time of the contrast agent through the region of interest is in a range of 6-7 seconds. In another example embodiment, the time period of the plateau region is in a range of 5-25 seconds.

In block 206, a plurality of parameters are determined for a functional form for a contrast injection function in a time domain. In some embodiments, the functional form is selected to conform to the manner in which the injection pump can be controlled, e.g., with a biphasic functional form for injection pumps programmable for two different durations each with a corresponding different but constant injection rate. Some injection pumps can be programmed for up to 6 different phases (each of variable duration and different constant injection rate).

Figure 4:
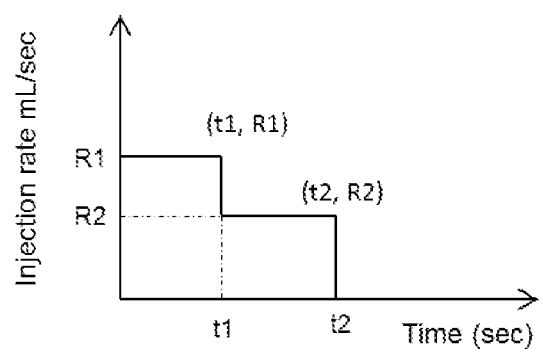
FIG. 4 illustrates an example of a multiphasic contrast injection function, according to one embodiment.

FIG. 4 illustrates an example of a contrast injection function, according to one embodiment, where the vertical axis is the rate of injection (in units of milliliters per second or ml/sec) and the horizontal axis is time (in units of seconds or sec). The contrast injection function is a biphasic injection function, which begins at time t=0 with a constant rate of injection $R_1$. At time $t_1$, the rate of injection is reduced from the constant rate of injection $R_1$ to a constant rate of injection $R_2$. At time $t_2$, the rate of injection is reduced from $R_2$ to 0. These are the parameters of the functional form of the injection function. In an illustrated embodiment, for purposes of determining the plurality of parameters for the functional form of the contrast injection function, the time domain between t=0 and $t_2$ is divided into discrete time periods. One parameter, x(t), for the functional form of the contrast rate injection is based on an integer variable and is a time for a change in the rate of injection at each discrete time period between t=0 and $t_2$. The integer variable is a binary integer variable selected from the domain {0, 1}. For those discrete time periods when there is no change in the rate of injection, the binary integer variable of the parameter x(t) is set to 0. For those discrete time periods when there is a change in the rate of injection, the binary integer variable of the parameter x(t) is set to 1. As depicted in FIG. 4, the times for the change in the rate of injection occur at $t_1$ (when the injection function changes from constant rate of injection $R_1$ to $R_2$) and at $t_2$ (when the injection function changes from constant rate of injection $R_2$ to zero). Thus the parameter of the time for a change in the rate of injection is based on an integer variable that is 1 for those discrete time periods corresponding to $t_1$ and $t_2$ and is 0 for all other discrete time periods between 0 and $t_2$.

Another parameter, y(t), for the functional form of the contrast rate injection is based on an integer variable and is a switch for the rate of injection at each discrete time period from before t=0 until after $t_2$. The integer variable is a binary integer variable selected from the domain {0, 1}. For those discrete time periods when the rate of injection is 0, the binary integer variable of the parameter y(t) is set to 0. For those discrete time periods when the rate of injection is greater than 0, the binary integer variable for the parameter y(t) is set to 1. As depicted in FIG. 4, the rate of injection is 0 before time 0 and at after time $t_2$ and is greater than 0 after time 0 and prior to time $t_2$. Thus the parameter y(t) of the switch for the rate of injection is based on an integer variable that is 0 for the discrete time periods corresponding to before 0 and after $t_2$ and is 1 for all other discrete time periods between 0 and $t_2$.

Although FIG. 4 depicts a biphasic injection function where the rate of injection changes twice over the duration of the injection function, the invention is not limited to biphasic injection functions and includes multiphase injection functions for which the parameters x(t) and y(t) above can be determined, using the same process previously discussed. In various embodiments the number of phases is selected between 2 and 6.

Figure 9:
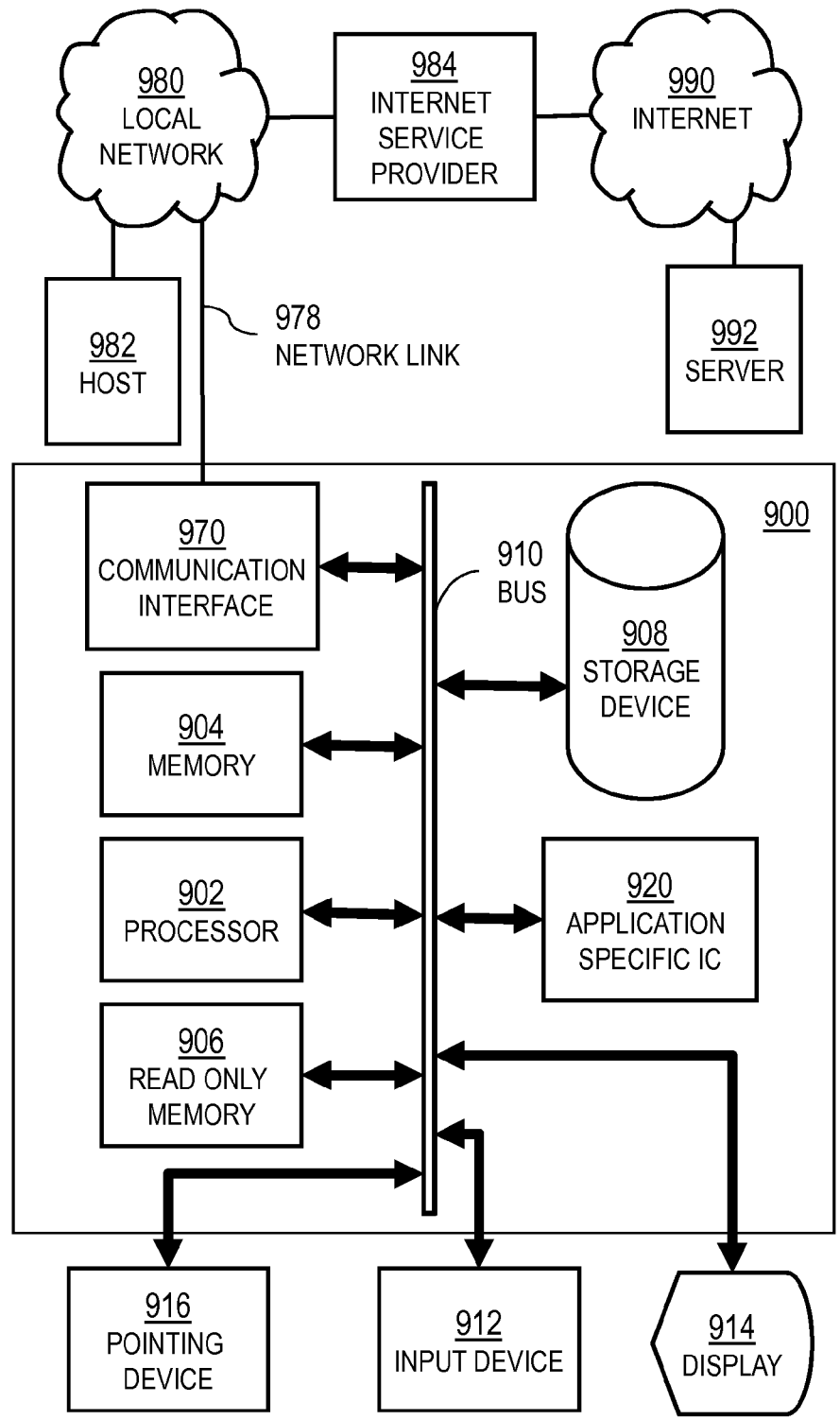
FIG. 9 is a block diagram that illustrates a computer system upon which an embodiment of the invention may be implemented.

In block 208, one or more constraints are determined for the contrast injection function. The constraints are based on practical and/or clinical limits of the contrast injection function. In some embodiments, one of the constraints is that the injector pump 102 can inject up to a maximum total contrast volume. A total contrast volume is defined as a sum of the rates of injection of the contrast injection function over all discrete time periods. In an example embodiment, the maximum total contrast agent volume is in a range between 65 milliliters and 130 milliliters. The contrast agent volume is represented as the area under the contrast injection function depicted in FIG. 4. In some embodiments the only or another constraint is that the injector pump 102 can perform up to a maximum number of changes in the rate of injection over the duration of the contrast injection function. In various embodiments, the maximum number of changes can be in a range between 2 and 6, depending on how many phases can be executed by the injection pump. In some embodiments, one constraint is that for each change in the rate of injection, the injector pump 102 can accommodate up to a maximum value for a change in the rate of injection. In an example embodiment, the maximum change in the rate of injection is approximately 5 milliliters per second. In some embodiments, one constraint is that the rate of injection (when y(t)=1) is within a range between a minimum value and a maximum value. In an example embodiment, the minimum value is selected within a range of 1.0-3.0 milliliters per second and in one embodiment is approximately 1.5 milliliters per second. In an example embodiment, the maximum value is selected within a range of 5.0-10.0 milliliters per second and in one embodiment is approximately 5 milliliters per second. In some embodiments, one constraint is that the rate of injection is greater than or equal to zero at all times, i.e., is never negative. In some embodiments, one constraint is that a maximum time duration of the contrast injection function is within an acceptable range of 30-60 seconds. In an example embodiment, one or more of these constraints are input by a user into the processor 108, such as with a keypad, or retrieved from a data file stored locally or accessed remotely through a network, as depicted in FIG. 9.

In block 210, an enhancement function is determined, based on the impulse enhancement function determined in block 202 and the contrast injection function. The enhancement function e(t) is defined as in Equation 2.

$$e(t)=h(t)*i(t) \qquad (2)$$

Where h(t) is the impulse enhancement function defined by Equation 1; i(t) is the contrast injection function, such as the biphasic injection function depicted in FIG. 4, with the parameters defined by block 206 and constraints defined by block 208 and * is a convolution operator. The enhancement function e(t) provides the radiodensity (in HU) of captured images from the ROI in the subject with the specific impulse enhancement function h(t) and who has been administered contrast agent based on the contrast injection function i(t).

In block 212, particular values are determined for the parameters determined in block 206, in order to satisfy the one or more constraints determined in block 208 and to minimize a difference between the enhancement function determined in block 210 and the target enhancement function determined in block 204. The difference between the enhancement function and the target enhancement function is computed and minimized in the time domain at discrete time periods without the use of a Fourier transform. Although a Fourier transform and inverse Fourier transform was used to determine the impulse enhancement function in block 202 using Equation 1, neither a Fourier transform nor an inverse Fourier transform is used in block 212 to minimize the difference between the enhancement function determined in block 210 and the target enhancement function determined in block 204. The difference is determined in the time domain over the plateau time region (beginning at $T_{arr}$) of the target enhancement function, when the target enhancement function is at the plateau level $E_1$.

In an example embodiment, the difference between the enhancement function and the target enhancement function is minimized using a mixed integer solution. As discussed above, in some embodiments, one of the parameters is a binary integer variables x(t), a time for a change in the rate of injection at each discrete time period between t=0 and $t_2$ in the contrast injection function of FIG. 4. Also, as discussed above, in some embodiments, one of the constraints is that the injector pump 102 can perform up to a maximum number of changes in the rate of injection over the duration of the contrast injection function. In block 212, the binary integer variable of the parameter x(t) is selected from the domain {0,1} for each discrete time period, so that the sum of the number of times for a change in the rate of injection does not exceed the constraint of the maximum number of changes and so that the difference between the enhancement function and the target enhancement function is minimized over the plateau time region. The selection of the values of the parameter x(t) may also be determined, so to satisfy one or more of the other constraints discussed above. For example, since the values of the parameter x(t) determine the discrete time periods when the rate of injection is reduced, these values affect the total contrast volume of the injection function and thus are selected such that the maximum contrast volume constraint is satisfied.

As discussed above, one of the parameters is a binary integer variable y(t), a switch for a rate of injection at each discrete time period from before t=0 until after $t_2$ in the contrast injection function of FIG. 4. In block 212, the binary integer variable of the parameter y(t) is selected from the domain {0,1} for each discrete time period, so that one or more of the constraints discussed above are satisfied and so that the difference between the enhancement function and the target enhancement function is minimized over the plateau time region. As discussed above, in some embodiments, one of the constraints is that the rate of injection is either zero or within a range between a minimum value and a maximum value. The values of the parameter y(t) at each discrete period are selected, so that the value of the rate of injection at each discrete time period is given by a product of the switch parameter y(t) and a value within the range between the minimum value and maximum value, thereby satisfying the above constraint. Another constraint satisfied during the selection of the values of the parameter y(t), in some embodiments, is that the total contrast volume of the contrast injection function is less than a maximum contrast agent volume. Since the selection of the values of the parameters y(t) affects the duration of the contrast injection, this selection affects the total contrast volume of the contrast injection function, and thus the values of y(t) are selected so to conform with this constraint.

In block 212, in the embodiments using binary integer variables x(t) and y(t), the processor 108 uses the mixed integer solution to efficiently search every possible combination of integer variables for the parameters x(t) and y(t) and continuous variable i(t) at each discrete time period, until the processor 108 determines the particular values of the integer variables for the parameters x(t) and y(t) at each discrete time period which satisfy the constraints and minimize the difference between the enhancement function and the target enhancement function over the plateau time region.

The mixed integer solution can be determined, based on one or more equations discussed below. In general, the difference between the value of the enhancement function and the target enhancement function is expressed as in Equation 3.

$$\Sigma_{t \in [|z(t), z(t) + T]} |h(t)*i(t) - E_1| \qquad (3)$$

wherein h(t) is the impulse enhancement function, i(t) is the contrast injection function, h(t)*i(t) is the enhancement function e(t), $E_1$ is the plateau level of the target enhancement function over the time domain, z(t) is the discrete time periods which extend a duration of T in the time domain, and * indicates the convolution operation. The time duration T is based on a duration of the plateau region of the target enhancement function. In an example embodiment, the time duration T is in a range of 5-25 seconds. In another example embodiment, the time duration T is in a range of 10-12 seconds.

The constraint of the maximum number of changes in the rate of injection over all discrete time periods can be expressed as in Equation 4.

$$\Sigma_t x(t) = A \quad (4)$$

wherein x(t) is the parameter based on the binary integer that is 0 at those discrete time periods when there is no change in the rate of injection and is 1 at those discrete time periods when there is a change in the rate of injection, and where A is the maximum number of changes in the rate of injection over all discrete time periods. Equation 4 ensures that the contrast injection function has A phases, where each phase has a fixed rate of injection. The number of phases of the contrast injection function can be adjusted, by changing the value of A. In an example embodiment, the maximum number of changes A is in a range between 2 and 6. In another example embodiment, the maximum number of changes A is 2. A value of 2 has the advantage that it is simpler to implement by a technician with fewer errors and is often sufficient to provide useful scans of the region of interest.

The constraint of the maximum extent of a change in the rate of injection between consecutive discrete time periods is expressed as in Equation 5.

$$0 \leq i(t) - i(t+B) \leq Cx(t) \quad (5)$$

where B is the discrete time period, C is the maximum extent of change between consecutive discrete time periods and x(t) is the parameter based on the binary integer that is 0 when there is no change in the rate of injection between consecutive discrete time periods and is 1 when there is a reduction in the rate of injection up to C. In an example embodiment, the discrete time period is 0.1 seconds and the maximum extent of change is approximately 5 milliliters per second. Equation 5 ensures that when the contrast injection function (depicted in FIG. 4) is not at times $t_1$ and $t_2$, it is at a constant rate and when the contrast injection function is at times $t_1$ and $t_2$, it is a step-down function where the rate of injection decreases by up to C.

The constraint on the value of the rate of injection at each discrete time period is expressed as in Equation 6.

$$Dy(t) \leq i(t) \leq Ey(t) \quad (6)$$

where D is the minimum value of the rate of injection and E is the maximum value of the rate of injection at each discrete time period, and y(t) is the parameter based on the binary integer that is 0 when the value of the rate of injection at each discrete time period is 0 and is 1 when the value of the rate of injection at each discrete time period is within the range between D and E. Equation 6 ensures that when the rate of injection is non-zero, it is in the range between D and E. In an example embodiment, the minimum value of the rate of injection D is approximately 1.5 milliliters per second and the maximum value of the rate of injection E is approximately 5 milliliters per second.

The constraints of the maximum contrast volume and the rate of injection being greater than or equal to zero are expressed as given by Equation 7.

$$\sum_i i(t) \leq V_{max} \text{ and } i(t) \geq 0 \quad (7)$$

where $V_{max}$ is the maximum contrast volume and i(t) is the contrast injection function. Equation 7 ensures that the rate of injection is positive or zero and that the total contrast volume is less than the maximum contrast volume. In an example embodiment, the maximum contrast volume is in a range between 65-130 milliliters for the example contrast agent. For other contrast agents other ranges for the maximum volume are applied. The maximum 130 is preferred for the illustrated embodiment as giving the most leeway for obtaining an optimal injection function.

After the user selects the constraints A-E and the maximum contrast volume $V_{max}$, the processor 108 is configured to determine the particular values of the integer variables for the parameters x(t) and y(t) at each discrete time period which satisfy the constraints (expressed in Equations 4-7) and minimizes the difference (expressed in Equation 3) between the enhancement function and the target enhancement function over the plateau time region. Although a plurality of constraints and parameters are discussed above, in an example embodiment, the processor 108 does not consider all of the above discussed constraints and parameters when determining the particular values of the integer variables for the parameter(s) and minimizing the difference between the enhancement function and the target enhancement function over the plateau time region.

In block 212, one or more stop conditions can cause the processor 108 to cease determining the values of the parameters. One stop condition occurs if the elapsed time for the processor 108 determination of the particular values of the parameters to minimize the difference between the enhancement function and the target enhancement function exceeds a maximum computation time. In an example embodiment, the maximum computation time is 120 seconds. In an example embodiment, the range of maximum computation time is 30-120 seconds. Another stop condition occurs if the difference between the enhancement function and the target enhancement function falls below a threshold error tolerance. In an example embodiment, the threshold error tolerance is 1%. In an example embodiment, the threshold error tolerance is in a range between 0-10%.

In block 214, the contrast agent is injected into the subject 190 using the injector pump 102, based on the contrast injection function determined using the particular values of the parameters determined in block 212. After waiting the initial time $T_{arr}$ discussed above for the contrast agent to reach the region of interest, then the scanner 106 commences to capture images of the region of interest and the processor 108 determines an enhancement function based on the contrast injection function. In an example embodiment, the scanner 106 commences to capture images after waiting the initial time $T_{arr}$ plus an additional time period, such as 5 seconds, for example. In an example embodiment, the additional time period is selected within a range of 3-7 seconds.

2. EXAMPLE EMBODIMENTS

Some embodiments of the invention are described in the context of a bi-phasic injection function. However, it should be understood that the method and apparatus of the present invention may be configured to perform a multi-phasic injection function which includes more than two phases. In an example embodiment, the injection function may have between 2 and 6 phases. One having ordinary skill in the art would recognize minor changes that would be necessary to adapt the system for different uses and different injection pumps. These modifications should be considered part of the invention because they do not deviate from its overall spirit.

In an example embodiment, during the method 200, the test bolus injected in block 201 is injected intravenously into the subject 190. The test bolus may be any agent known in the art, including, but not limited to Iohexol Omnipaque 350. The amount of contrast agent injected in block 201 may range from approximately 5 milliliters to approximately 30 milliliters. In an example embodiment, the total volume of test bolus contrast agent will be between approximately 10 milliliters and 20 milliliters. In another example embodiment, the volume of the test bolus contrast agent is approximately 20 milliliters. In an example embodiment, the rate of injection of the test injection function may range from about 0.5 milliliters per second to approximately 15 milliliters per second. In an example embodiment, the volume flow rate of the test injection function is approximately 5 milliliters per second.

As the test bolus is injected in block 201, the test enhancement function is determined, based on CT images repeatedly taken by the scanner 106 of the ROI. FIG. 5A illustrates an example of a CT image of the ROI in a pulmonary artery, according to one embodiment. In some embodiments the images may be taken every $T_0$ seconds, where $T_0$ may range from about 1 second to about 5 seconds. In other embodiments, the images may be taken more or less frequently. Images are taken in block 201 until after the peak enhancement of the ROI is achieved. The test enhancement function depicted in FIG. 5B is determined by using a piecewise curve fitting method which fits those test sample points prior to the peak enhancement to a rising part and fits those test sample points after the peak enhancement to a falling part. In some examples, the falling or washing-out portion of the enhancement function can be estimated by fitting the test enhancement function to an exponential function using the "fininsearch" function in MATLAB® (The MathWorks, Inc., Natick, Mass.). Other known functions and software programs may be used in place of MATLAB®, including but not limited to Mathematica® (Wolfram Research, Campaign, Ill.) or GNU Octave®. Alternatively, the test enhancement function depicted in FIG. 5B can be determined by fitting a skew normal curve to all test sample points as a whole, which preserves the peak enhancement level of the test enhancement function. In other example methods, the test enhancement function may be used without fitting.

In one example embodiment, to determine the target enhancement function in block 204, only the plateau level $E_1$ of the targeted enhancement function is specified. In an example embodiment, the plateau level $E_1$ may be between approximately 50 HU and 500 HU. In some embodiments the plateau level $E_1$ is between approximately 200 HU and 300 HU. The plateau level $E_1$ may occur at the initial time $T_{arr}$ that is between approximately 5 seconds and 60 seconds after initiation of the contrast injection. In some embodiments the plateau level $E_1$ occurs at an initial time $T_{arr}$ of approximately 10 seconds.

In an example embodiment, in block 208, the maximum contrast volume constraint is in a range of 65 milliliters to 130 milliliters. In an example embodiment, a maximum injection time may be a constraint. Those having skill in the art would recognize other constraints that may improve the optimized injection function.

In an example embodiment, twenty seven patients were retrospectively selected who had CTPA scans within a two week interval in 2012 in the Department of Diagnostic Radiology and Nuclear Medicine at University of Maryland Medical Center. This cohort consisted of 19 men and 8 women, with a mean age 46 years (range 17-82 years). All patients were scanned on either a Philips iCT 256 slice scanner or a Philips Brilliance 64 slice scanner. The CTPA scanning protocol starts with a frontal and lateral scout scans obtained from apices to mid-renal. This is followed by a test bolus scan with 20 milliliters of contrast agent and a simulated bolus scan with 65 milliliters of contrast agent. The contrast agent (Omnipaque 350) is injected intravenously at a constant rate of 5 milliliters per second for all patients. In the test bolus scan, a fixed longitudinal level of the patient is repeatedly imaged using a low dose (100 kVp, 100 mAs) axial technique. Table 1 shows a summary of the scan parameters for the test bolus scan and the simulated bolus scan, based on a body mass index (BMI) of the patient:

TABLE I

| | Test Bolus Scan | | Simulated Bolus Scan | |
|---|---|---|---|---|
| | BMI < 30 | BMI > 30 | BMI < 30 | BMI > 30 |
| kVp | 100 | 120 | 100 | 120 |
| mAs | 50 | 100 | 150-330 | 200-488 |

This level is chosen to include the pulmonary artery (PA) in the image and a fixed circular region of interest (ROI) is drawn in the center of the PA. Once the ROI is drawn, the test bolus with a 20 mL of contrast is injected. Coinciding with the initiation of the injection, an axial CT image is acquired and repeated every two seconds until shortly after the peak enhancement of the ROI is achieved. The time to peak enhancement, or the initial time $^{T}arr$, is charted by the CT scanner 106 and recorded by the technologist. After the peak enhancement time $T_{arr}$ of the test bolus scan is determined, the simulated CTPA scan is performed following the simulated injection with a 65 mL contrast volume.

Once all the test injection axial images were acquired, a circular ROI of 3 cm$^2$ was placed in the PA, see FIG. 5A, and the test enhancement function (unit: HU) was measured within the ROI on each image. FIG. 5B shows the test enhancement function, which is a plot of the radiodensity or average CT number (in units of HU) of the captured images as a function of elapsed time from the administration of contrast. A baseline determined by the average CT number of the first three slices is subtracted from the test enhancement function, as the contrast has not arrived to the ROI in the first few seconds. In an example embodiment, the baseline can be determined by adaptively calculating the baseline level from the entire baseline region, such as during the first 7 seconds after the injection of the contrast.

In block 202 of the method 200, the patient impulse enhancement function (IEF) is determined. The patient IEF of a 0.1-sec increment 1 mL/sec injection was extracted from the test enhancement function, enabling the optimization of the contrast injection function with time accuracy up to 0.1 sec. In block 202, $^i{}_T(t)$ and $^1{}_T(f)$=FT($^i{}_T(t)$) denote the test injection function in the time and frequency domain, respectively, where FT(•) denotes the Fourier transform of a function. $e_T(t)$ and $E_t(f)$ are denoted for the test enhancement functions, and h(t) and H(f) for the patient IEFs.

As the patient enhancement curve to an injection function follows a linear, time invariant (LTI) system, $$H(f) = \frac{E_T(f)}{I_T(f)}. \tag{8}$$

To make this frequency division more stable, the amplitude less than 1.0E-06 in $1_T(f)$ was substituted by a non-zero small value 1.0E-06. A low-pass filter with a cutoff frequency of 0.125 Hz was further applied on H(f) to smooth the IEF. This is validated by the fact that the patient tends to be a low-pass system, i.e., the patient enhancement changes gradually with time.

In block 204, the target enhancement function is determined. Only the plateau region of the target enhancement function was specified for purposes of determining the contrast injection function in blocks 210, 212. The plateau level $E_1$ was chosen to be $E_1=300$ HU for the CT scans to be of diagnostic image quality. A time $T_{PTT}$ (see FIG. 5E) of 10-sec was used for the contrast agent to traverse the pulmonary blood vessels with a 2-3 second time margin. For those patients whose peak enhancement of the simulated enhancement function did not reach 300 HU, $E_1$ is reduced to a lower level, e.g., 200 HU, according to the peak enhancement of the simulated enhancement function over the minimum time period, as discussed in block 204.

In block 210, the continuous time was discretized into discrete time periods of 0.1 second intervals, and indexed using t=(0,0.1, . . . , T) (s), where T is the total injection duration (which is limited to 60 seconds). Equation 3 minimizes the sum of absolute difference between the enhancement function and target enhancement function. Two binary functions $x(t), y(t) \in \{0,1\}$ were introduced to control the changing points between two adjacent phases and the range of injection rate i(t), respectively. In Equation 5, if x(t)=0, there is no flow rate change from t to t+0.1 sec; if x(t)=1, the flow rate may reduce by an amplitude less than 5 mL/s. Since the summation of x(t) is A in Equation 4, then where A=2, a bi-phasic injection function is defined, as 2 changing points are provided: one between the two phases $R_1, R_2$ and another at the end of injection.

Binary function y(t) ensures that the injection rate is either in the range of 1.5-5 mL/sec or zero in Equation 6. Adding the constraints of the limit of total contrast volume $V_{max}$ and the non-negativity of i(t) in Equation 7, the optimization problem can be summarized in Equations 3-7.

In Equation 3, h(t)*i(t), the convolution of the IEF h(t) with the injection function i(t), denotes the enhancement function e(t) corresponding to i(t). Another variable, z(t), is used in Equation 3 to control the starting time of the 10-sec target enhancement interval. The overall mathematical model is formulated as a mixed integer program (MIP). It is solved using a powerful commercial solver, CPLEX Optimizer (International Business Machines, Armonk, N.Y.). The advantage of formulating the problem using MIP, which is an exact optimization approach, is that it guarantees the optimal solution if the problem is feasible.

The contrast injection function is optimized to produce the enhancement function that best achieves the targeted enhancement function within the given constraints. The uniformity of the target enhancement function and the maximum contrast volume constraint are competing with each other in the optimization process. In other words, to achieve the closest enhancement function to the plateau level E1 of the target enhancement function, more contrast will often be used. In an example embodiment, the maximum total volume constraint is in a range of 65 ml-130 ml. In an example embodiment, the injector pump 102 has a total volume which includes the total volume of the test bolus injection and the total volume of the contrast injection function. In an example embodiment, the injector pump 102 has a total volume of 150 ml, the total volume of the test bolus injection is approximately 20 ml and thus the maximum total volume of the contrast injection function is up to 130 ml that remains in the injector pump 102 after the test bolus injection.

The same patient set and data that was used in example embodiment discussed above was used in a second example embodiment using the DFT approach. Before the individual bi-phasic injection function of the DFT approach is designed, the target enhancement function is defined and is defined as $e_{IDFT}(t)$. The DFT approach employed an isosceles trapezoid shaped enhancement curve as the target enhancement function, which is depicted in FIG. 5E, which illustrates an example of a target enhancement function, according to one embodiment. The target enhancement function has a 10 second plateau enhancement region from $T_{arr}$ to $T_{arr}+T_{ptt}$, a 6 second rising region and an 8 second washing-out region before and after the plateau region. $E_1$ is the plateau level and $T_{PTT}$ (pulmonary transit time) is the targeted enhancement duration.

The target enhancement level was chosen to be $E_I=300$ HU for the CT scans to be of diagnostic image quality. A 10-sec $T_{ptt}$ was used for the contrast to traverse the pulmonary blood vessels with 2-3 second time margin. For patients with difficulty reaching 300 HU, $E_I$ is reduced to a lower level, e.g., 200 HU, according to the simulated full bolus enhancement function.

Figure 6A:
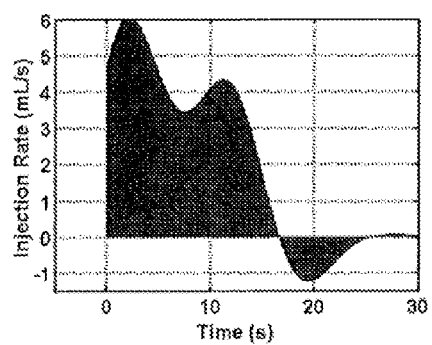
FIG. 6A illustrates an example of a contrast injection function, according to the DFT approach.

In the DFT approach, an "ideal" bolus injection function $i_I(t)$ is first computed by $$I_I(f) = \frac{E_{LDFT}(f)}{H(f)} \quad (9)$$

followed by an inverse Fourier transform of $I_I(f)$, where $E_{LDFT}(f)=FT(e_{iDFT}(t))$ and where H(f) is the IEF in the frequency domain. The ideal DFT injection function $i_I(t)$ is depicted in FIG. 6A, which illustrates an example of a contrast injection function, according to the DFT approach. The vertical axis of FIG. 6A is the rate of injection (in units of milliliters per second) and the horizontal axis is time (in units of seconds).

Figure 6B:
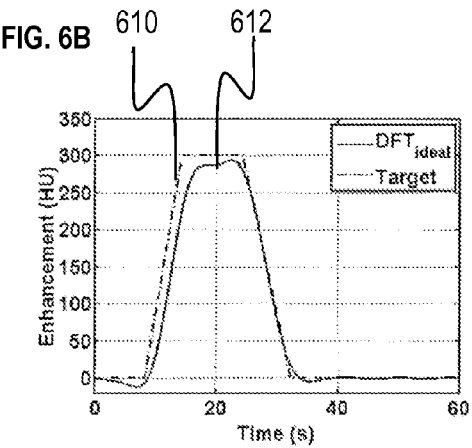
FIG. 6B illustrates an example of an enhancement function based on the contrast injection function of FIG. 6A and a target enhancement function, according to the DFT approach.
Figure 6C:
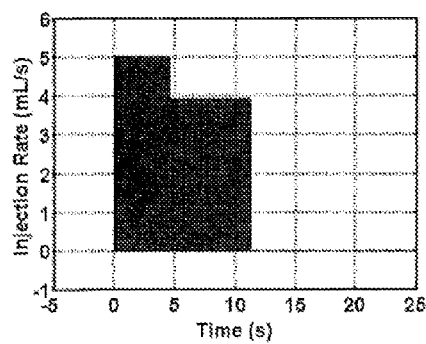
FIG. 6C illustrates an example of a biphasic contrast injection function, according to the DFT approach.
Figure 6D:
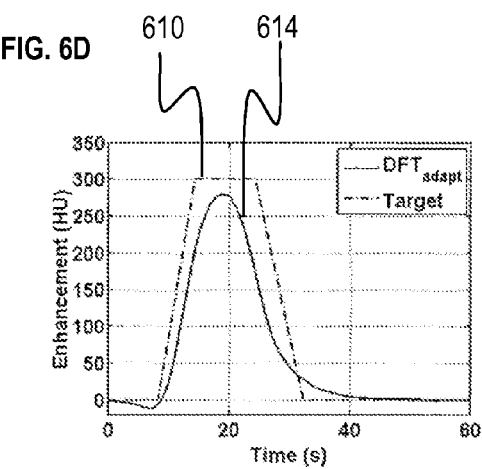
FIG. 6D illustrates an example of an enhancement function based on the contrast injection function of FIG. 6C and a target enhancement function, according to the DFT approach.

FIG. 6B illustrates an example of an enhancement function 612 based on the contrast injection function of FIG. 6A and a target enhancement function 610, according to the DFT approach. Note that $i_1(t)$ depicted in FIG. 6A is by nature continuously changing with time, and it may even become negative to accommodate the abrupt change in the washing-out part of the enhancement function 612. As current injector pumps cannot implement a continuously changing injection function and negative flow is unrealistic, the DFT approach uses an algorithm with heuristic parameters to adapt $i_1(t)$ to a bi-phasic one that best approximates $i_1(t)$. FIG. 6C illustrates an example of a resulting biphasic contrast injection function, according to the DFT approach. The vertical axis of FIG. 6C is the rate of injection (in units of milliliters per second) and the horizontal axis is time (in units of seconds). FIG. 6D illustrates an example of an enhancement function 614 based on the contrast injection function of FIG. 6C and a target enhancement function 610, according to the DFT approach. As shown by comparing FIGS. 6B and 6D, the adapted bi-phasic contrast injection function in the DFT approach degraded the enhancement function 614, showing large deviations with the target enhancement function 610.

The following criteria were used to evaluate the designed bi-phasic injection functions: 1) Root mean square error (RMSE) between the enhancement function resulting from the bi-phasic injection function and the target enhancement function, evaluated in the targeted 10-sec duration. 2) The total volume of contrast used. RMSEs of the DFT approach to those of the optimization approaches with either $V_{max}$=65 mL or $V_{max}$=$V_{DFT}$ were compared using paired student t-test at a significance level of 0.05.

The fitted test enhancement function is shown in FIG. 5B as a solid line. This fitted enhancement function is used to extract the patient IEF, which is shown in FIG. 5C. A simulated enhancement function using 65 mL contrast at a fixed injection rate of 5 mL/sec is plotted in FIG. 5D, where its peak enhancement level can help predict the targeted enhancement level for the bi-phasic injection function design.

Figure 7A:
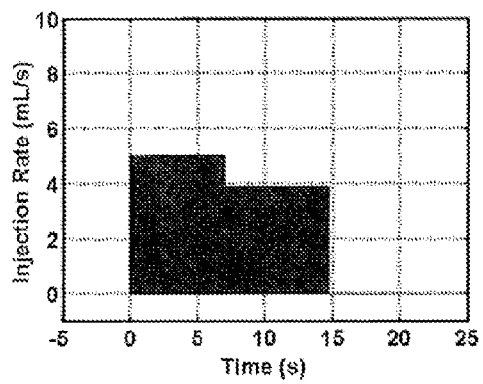
FIG. 7A illustrates an example of a contrast injection function, according to one embodiment.
Figure 7B:
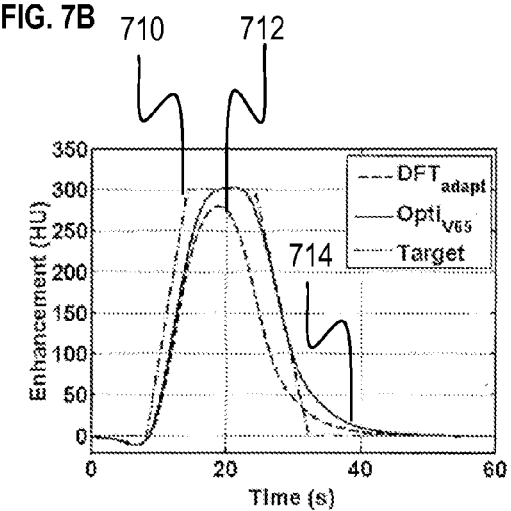
FIG. 7B illustrates an example of an enhancement function based on the contrast injection function of FIG. 7A, an enhancement function based on the DFT approach and a target enhancement function, according to one embodiment.

FIG. 7A illustrates an example of a biphasic contrast injection function, according to one embodiment. FIG. 7B illustrates an example of an enhancement function 714 based on the contrast injection function of FIG. 7A, an enhancement function 712 based on the DFT approach and a target enhancement function 710, according to one embodiment. When the contrast volume is limited by $V_{max}$=65 mL, the optimal bi-phasic injection function, the resulting enhancement function 712 for the DFT approach and the resulting enhancement function 714 for the optimization approach are shown in FIG. 7B. As shown in FIG. 7B, the enhancement function 714 for the optimization approach is more uniform and closely matched to the target enhancement function 710 of 300 HU than the enhancement function 712 of the DFT approach (RMSE 29 HV vs. 58 HU). In this example, all of the 65 mL contrast is used.

Figure 7C:
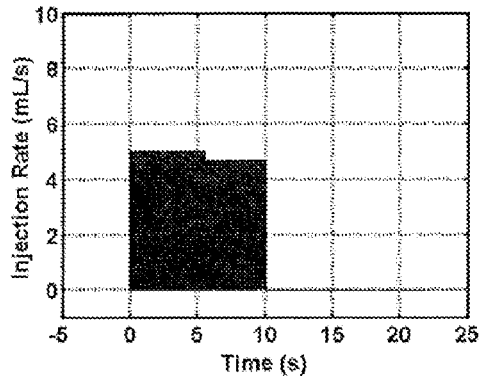
FIG. 7C illustrates an example of a biphasic contrast injection function, according to one embodiment.
Figure 7D:
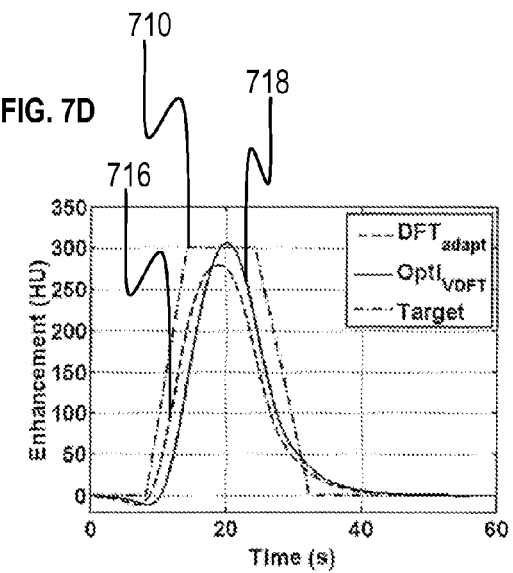
FIG. 7D illustrates an example of an enhancement function based on the contrast injection function of FIG. 7C, an enhancement function based on the DFT approach and a target enhancement function, according to one embodiment.

FIG. 7C illustrates an example of a biphasic contrast injection function, according to one embodiment. FIG. 7D illustrates an example of an enhancement function 718 based on the contrast injection function of FIG. 7C, an enhancement function 716 based on the DFT approach and a target enhancement function 710, according to one embodiment. To compare the DFT approach and the optimization approach with the same amount of contrast, a new injection function was generated (see FIG. 7C) with the constraint that the total contrast volume to be used is no more than that in the DFT approach. The corresponding enhancement function 718 of the optimization approach is more closely matched to the target enhancement function 710 than the enhancement function 716 of the DFT approach. With the same contrast volume, the results of the optimization approach are significantly better than those of the DFT approach, although not as good as when $V_{max}$=65 ml.

Figure 8B:
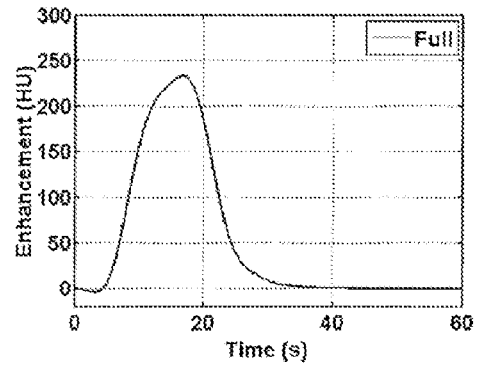
FIG. 8B illustrates an example of a simulated enhancement function based on the simulated injection function of FIG. 8A, according to one embodiment.
Figure 8C:
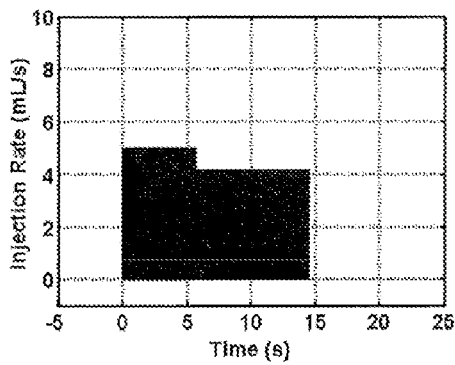
FIG. 8C illustrates an example of a contrast injection function, according to one embodiment.
Figure 8D:
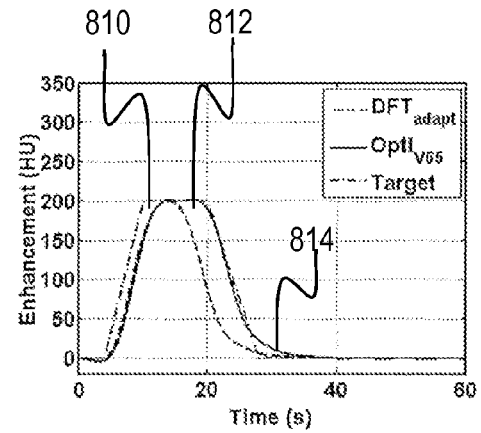
FIG. 8D illustrates an example of an enhancement function based on the contrast injection function of FIG. 8C, an enhancement function based on the DFT approach and a target enhancement function, according to one embodiment.

FIG. 8A illustrates an example of a simulated injection function, according to one embodiment. FIG. 8B illustrates an example of a simulated enhancement function based on the simulated injection function of FIG. 8A, according to one embodiment. In 11 of the 27 patients, the optimization approach cannot reach the targeted enhancement level of 300 HU. This is depicted from the simulated full bolus (65 mL at constant rate of 5 mL/sec) enhancement function in FIG. 8B, where the peak is apparently below 300 HU. Therefore, the target enhancement level was reduced to a lower value, e.g., 200 HU, based on a maximum value maintained by the simulated enhancement function over a minimum time period, as discussed in block 204 of method 200.

In Table II, the total contrast volume V and the RMSE are listed for the 27 patients using three designs: $V_{opti}$ and $RMSE_{opti}$ as the volume and RMSE for the optimization method using $V_{max}$=65 mL; $V_{DFT}$ and $RMSE_{DFT}$ for the DFT method; and $RMSE_{opti.DFT}$ as the RMSE for optimization method with total contrast volume constrained to be no more than that in DFT method. The mean RMSE for the optimization approach with $V_{max}$=65 mL is 17 HU, which is significantly lower than the mean RMSE of 56 HU for the DFT approach (p<0.00001). From Table II, it is noted in the optimization approach with $V_{max}$=65 mL, 24 out of 27 patients use all the given contrast with mean volume of 63 mL. On the other hand, in the DFT approach, only 4 of the 27 patients use more than 65 mL contrast with mean volume of 50 mL. When using the same amount of contrast, it is depicted in FIG. 7D and Table II that the optimization approach still generates more uniform enhancement than the DFT approach, with a mean RMSE of 44 HU compared to that of 56 HU for the DFT approach (p<0.01).

TABLE II

| Patient # | Targeted Enh. Level (HU) | Opti. w/$V_{max}$ = 65 mL | | DFT approach | | Opti. w/$V_{max}$ = $V_{DFT}$ | |
|---|---|---|---|---|---|---|---|
| | | V (mL) | RMSE (HU) | V (mL) | RMSE (HU) | V (mL) | RMSE (HU) |
| 1 | 300 | 32 | 10 | 26 | 45 | 26 | 38 |
| 2 | 200 | 65 | 14 | 49 | 42 | 49 | 41 |
| 3 | 250 | 65 | 32 | 46 | 76 | 46 | 62 |
| 4 | 300 | 65 | 17 | 45 | 67 | 45 | 72 |
| 5 | 300 | 65 | 44 | 51 | 79 | 51 | 80 |
| 6 | 300 | 65 | 12 | 43 | 66 | 43 | 71 |
| 7 | 300 | 65 | 40 | 48 | 96 | 48 | 89 |
| 8 | 150 | 65 | 19 | 81 | 29 | 81 | 6 |
| 9 | 250 | 65 | 20 | 76 | 51 | 76 | 6 |
| 10 | 50 | 50 | 5 | 33 | 11 | 33 | 12 |
| 11 | 300 | 65 | 30 | 79 | 59 | 79 | 8 |
| 12 | 300 | 65 | 18 | 47 | 59 | 47 | 63 |
| 13 | 300 | 65 | 48 | 47 | 91 | 47 | 96 |
| 14 | 100 | 65 | 11 | 44 | 33 | 44 | 33 |
| 15 | 300 | 65 | 4 | 48 | 37 | 48 | 33 |
| 16 | 250 | 65 | 18 | 46 | 76 | 46 | 36 |
| 17 | 150 | 65 | 14 | 46 | 37 | 46 | 40 |
| 18 | 300 | 65 | 3 | 38 | 59 | 38 | 50 |
| 19 | 300 | 65 | 0 | 49 | 57 | 49 | 11 |
| 20 | 300 | 65 | 11 | 40 | 80 | 40 | 83 |
| 21 | 300 | 61 | 1 | 37 | 48 | 37 | 43 |
| 22 | 150 | 65 | 4 | 39 | 42 | 39 | 41 |
| 23 | 150 | 65 | 4 | 62 | 34 | 62 | 6 |
| 24 | 300 | 65 | 29 | 54 | 58 | 54 | 56 |
| 25 | 200 | 65 | 11 | 43 | 49 | 43 | 54 |
| 26 | 300 | 65 | 28 | 79 | 64 | 79 | 4 |
| 27 | 300 | 65 | 26 | 49 | 60 | 49 | 65 |
| Mean | 248 | 63 | 17 | 50 | 56 | 50 | 44 |

In modern CT scans, it becomes more important to adjust the contrast injection according to each patient's unique IEF determined in block 202 of the method 200. By exploiting the patient IEF extracted from the test bolus injection, the patient's enhancement function can be predicted, in response to any contrast injection function. Given the patient's IEF, an optimal search was performed directly in the time domain to find the optimal bi-phasic injection function that can achieve the enhancement function that has minimal difference with the target enhancement function in the plateau region while also satisfying the constraints. From FIGS. 7A-7D, FIGS. 8A-8D and Table II, the optimization approach designs optimal bi-phasic injection functions that result in more uniform enhancement in the plateau region of the target enhancement function with much smaller RMSE than the previously reported DFT approach. This optimization can incorporate constraints such as the maximum injection rate and maximum contrast volume while searching for the optimal design.

The DFT method suffers from several problems that are inherent in the implementation. First, the "ideal" bolus injection function is generated without constraints that are used for the bi-phasic adaptation. Therefore, the function is continuously changing with time, and there is negative flow rate involved as shown in FIG. 6A. This negative injection is a result of the abrupt falling-down in the washing-out part of the ideal enhancement function. Because the human system, which is described by the patient IEF, cannot fall down as quickly as the ideal enhancement function h(t)*i(t) in Equation 3, the negative injection rate appears as an effort to pull down the enhancement function quickly enough to conform to the target enhancement function. Second, the adaptation from the ideal injection function (FIG. 6A) to the bi-phasic injection function (FIG. 6B) is based on empirical parameters. In the adaptation, more constraints are added to the injection function, and this resulted in further deviation of the enhancement function from the targeted enhancement function, as shown in FIG. 6D. Therefore, optimality is not guaranteed in DFT approach, which is reflected in the large deviations from the targeted enhancement function, as shown in FIG. 6D and Table II. In addition, as there are frequency coefficients divisions involved, whenever there are zero or near-zero values in the denominator, the DFT method tends to become unstable.

On the other hand, for the optimization approach, constraints are naturally taken into consideration while searching the optimal bi-phasic injection function. Therefore the generated contrast injection function is by design the optimal one under the given constraints. The much improved enhancement function in the optimization approach is mainly due to the advantage of optimization algorithm. Under the same constraints, Table II indicates that most of the patients used the maximum contrast volume $V_{max}=65$ mL in the optimization design, while in the DFT approach only 4 patients exceed 65 mL. The optimization approach is able to use more contrast medium that produces a more uniform enhancement function compared to the DFT approach (RMSE 17 HU v.s. 56 HU, p<0.00001). To eliminate the contrast volume difference between these two approaches, the same amount of contrast as the DFT approach was used in the optimization approach, as shown in Table II. However, even with the same contrast volume, the optimization approach still achieves significantly more uniform enhancement (RMSE: 44 HU v.s. 56 HU, p<0.0099). This implies that the optimization approach uses the contrast more efficiently in generating the desired enhancement function, and thus potentially avoiding non-diagnostic CT image quality due to insufficient contrast volume. Although the optimization approach provides satisfactory enhancement results for most of the patients, not all the patients can achieve the 300 HU targeted enhancement level. Particularly, 6 patients in the sample only achieved an enhancement level <200 HU. The plateau level of the targeted enhancement function is set so that it can be reached if all of the 65 mL contrast is injected at a constant rate of 5 mL/sec, in the simulated bolus injection. In the test enhancement function, these patients are characterized by low peak enhancement and quick washing-out of the test enhancement function after the peak enhancement. Large patient habitus and fast cardiac output are two possible contributing factors for the low enhancement level. In this study, the targeted enhancement level is reduced to a lower realistic value for these patients, as shown in the plateau level of the target enhancement function 810 of FIG. 8D, so that both the DFT and the optimization approaches can achieve the plateau level of the target enhancement function under the injection constraints such as injection rate and contrast volume. However, higher injection rates and more contrast volume may be used for these patients, if deemed safe by physicians, to provide better contrast-enhanced CT images.

As illustrated in the enhancement functions depicted in FIGS. 5-8, the enhancement functions initially go down in an initial time period before rising up to a peak enhancement level. The reason is that saline solution is injected into the patient before the bolus injection and residual saline in the injection tube may have diluted the blood so that the CT number drops off before the contrast arrives.

3. COMPUTATIONAL HARDWARE OVERVIEW

FIG. 9 is a block diagram that illustrates a computer system 900 upon which an embodiment of the invention may be implemented. Computer system 900 includes a communication mechanism such as a bus 910 for passing information between other internal and external components of the computer system 900. Information is represented as physical signals of a measurable phenomenon, typically electric voltages, but including, in other embodiments, such phenomena as magnetic, electromagnetic, pressure, chemical, molecular atomic and quantum interactions. For example, north and south magnetic fields, or a zero and non-zero electric voltage, represent two states (0, 1) of a binary digit (bit). Other phenomena can represent digits of a higher base. A superposition of multiple simultaneous quantum states before measurement represents a quantum bit (qubit). A sequence of one or more digits constitutes digital data that is used to represent a number or code for a character. In some embodiments, information called analog data is represented by a near continuum of measurable values within a particular range. Computer system 900, or a portion thereof, constitutes a means for performing one or more steps of one or more methods described herein.

A sequence of binary digits constitutes digital data that is used to represent a number or code for a character. A bus 910 includes many parallel conductors of information so that information is transferred quickly among devices coupled to the bus 910. One or more processors 902 for processing information are coupled with the bus 910. A processor 902 performs a set of operations on information. The set of operations include bringing information in from the bus 910 and placing information on the bus 910. The set of operations also typically include comparing two or more units of information, shifting positions of units of information, and combining two or more units of information, such as by addition or multiplication. A sequence of operations to be executed by the processor 902 constitutes computer instructions.

Computer system 900 also includes a memory 904 coupled to bus 910. The memory 904, such as a random access memory (RAM) or other dynamic storage device, stores information including computer instructions. Dynamic memory allows information stored therein to be changed by the computer system 900. RAM allows a unit of information stored at a location called a memory address to be stored and retrieved independently of information at neighboring addresses. The memory 904 is also used by the processor 902 to store temporary values during execution of computer instructions. The computer system 900 also includes a read only memory (ROM) 906 or other static storage device coupled to the bus 910 for storing static information, including instructions, that is not changed by the computer system 900. Also coupled to bus 910 is a non-volatile (persistent) storage device 908, such as a magnetic disk or optical disk, for storing information, including instructions, that persists even when the computer system 900 is turned off or otherwise loses power.

Information, including instructions, is provided to the bus 910 for use by the processor from an external input device 912, such as a keyboard containing alphanumeric keys operated by a human user, or a sensor. A sensor detects conditions in its vicinity and transforms those detections into signals compatible with the signals used to represent information in computer system 900. Other external devices coupled to bus 910, used primarily for interacting with humans, include a display device 914, such as a cathode ray tube (CRT) or a liquid crystal display (LCD), for presenting images, and a pointing device 916, such as a mouse or a trackball or cursor direction keys, for controlling a position of a small cursor image presented on the display 914 and issuing commands associated with graphical elements presented on the display 914.

In the illustrated embodiment, special purpose hardware, such as an application specific integrated circuit (IC) 920, is coupled to bus 910. The special purpose hardware is configured to perform operations not performed by processor 902 quickly enough for special purposes. Examples of application specific ICs include graphics accelerator cards for generating images for display 914, cryptographic boards for encrypting and decrypting messages sent over a network, speech recognition, and interfaces to special external devices, such as robotic arms and medical scanning equipment that repeatedly perform some complex sequence of operations that are more efficiently implemented in hardware.

Computer system 900 also includes one or more instances of a communications interface 970 coupled to bus 910. Communication interface 970 provides a two-way communication coupling to a variety of external devices that operate with their own processors, such as printers, scanners and external disks. In general the coupling is with a network link 978 that is connected to a local network 980 to which a variety of external devices with their own processors are connected. For example, communication interface 970 may be a parallel port or a serial port or a universal serial bus (USB) port on a personal computer. In some embodiments, communications interface 970 is an integrated services digital network (ISDN) card or a digital subscriber line (DSL) card or a telephone modem that provides an information communication connection to a corresponding type of telephone line. In some embodiments, a communication interface 970 is a cable modem that converts signals on bus 910 into signals for a communication connection over a coaxial cable or into optical signals for a communication connection over a fiber optic cable. As another example, communications interface 970 may be a local area network (LAN) card to provide a data communication connection to a compatible LAN, such as Ethernet. Wireless links may also be implemented. Carrier waves, such as acoustic waves and electromagnetic waves, including radio, optical and infrared waves travel through space without wires or cables. Signals include man-made variations in amplitude, frequency, phase, polarization or other physical properties of carrier waves. For wireless links, the communications interface 970 sends and receives electrical, acoustic or electromagnetic signals, including infrared and optical signals that carry information streams, such as digital data.

The term computer-readable medium is used herein to refer to any medium that participates in providing information to processor 902, including instructions for execution. Such a medium may take many forms, including, but not limited to, non-volatile media, volatile media and transmission media. Non-volatile media include, for example, optical or magnetic disks, such as storage device 908. Volatile media include, for example, dynamic memory 904. Transmission media include, for example, coaxial cables, copper wire, fiber optic cables, and waves that travel through space without wires or cables, such as acoustic waves and electromagnetic waves, including radio, optical and infrared waves. The term computer-readable storage medium is used herein to refer to any medium that participates in providing information to processor 902, except for transmission media.

Common forms of computer-readable media include, for example, a floppy disk, a flexible disk, a hard disk, a magnetic tape, or any other magnetic medium, a compact disk ROM (CD-ROM), a digital video disk (DVD) or any other optical medium, punch cards, paper tape, or any other physical medium with patterns of holes, a RAM, a programmable ROM (PROM), an erasable PROM (EPROM), a FLASH-EPROM, or any other memory chip or cartridge, a carrier wave, or any other medium from which a computer can read. The term non-transitory computer-readable storage medium is used herein to refer to any medium that participates in providing information to processor 902, except for carrier waves and other signals.

Logic encoded in one or more tangible media includes one or both of processor instructions on a computer-readable storage media and special purpose hardware, such as ASIC 920.

Network link 978 typically provides information communication through one or more networks to other devices that use or process the information. For example, network link 978 may provide a connection through local network 980 to a host computer 982 or to equipment 984 operated by an Internet Service Provider (ISP). ISP equipment 984 in turn provides data communication services through the public, world-wide packet-switching communication network of networks now commonly referred to as the Internet 990. A computer called a server 992 connected to the Internet provides a service in response to information received over the Internet. For example, server 992 provides information representing video data for presentation at display 914.

The invention is related to the use of computer system 900 for implementing the techniques described herein. According to one embodiment of the invention, those techniques are performed by computer system 900 in response to processor 902 executing one or more sequences of one or more instructions contained in memory 904. Such instructions, also called software and program code, may be read into memory 904 from another computer-readable medium such as storage device 908. Execution of the sequences of instructions contained in memory 904 causes processor 902 to perform the method steps described herein. In alternative embodiments, hardware, such as application specific integrated circuit 920, may be used in place of or in combination with software to implement the invention. Thus, embodiments of the invention are not limited to any specific combination of hardware and software.

The signals transmitted over network link 978 and other networks through communications interface 970, carry information to and from computer system 900. Computer system 900 can send and receive information, including program code, through the networks 980, 990 among others, through network link 978 and communications interface 970. In an example using the Internet 990, a server 992 transmits program code for a particular application, requested by a message sent from computer 900, through Internet 990, ISP equipment 984, local network 980 and communications interface 970. The received code may be executed by processor 902 as it is received, or may be stored in storage device 908 or other non-volatile storage for later execution, or both. In this manner, computer system 900 may obtain application program code in the form of a signal on a carrier wave.

Various forms of computer readable media may be involved in carrying one or more sequence of instructions or data or both to processor 902 for execution. For example, instructions and data may initially be carried on a magnetic disk of a remote computer such as host 982. The remote computer loads the instructions and data into its dynamic memory and sends the instructions and data over a telephone line using a modem. A modem local to the computer system 900 receives the instructions and data on a telephone line and uses an infra-red transmitter to convert the instructions and data to a signal on an infra-red a carrier wave serving as the network link 978. An infrared detector serving as communications interface 970 receives the instructions and data carried in the infrared signal and places information representing the instructions and data onto bus 910. Bus 910 carries the information to memory 904 from which processor 902 retrieves and executes the instructions using some of the data sent with the instructions. The instructions and data received in memory 904 may optionally be stored on storage device 908, either before or after execution by the processor 902.

Figure 10:
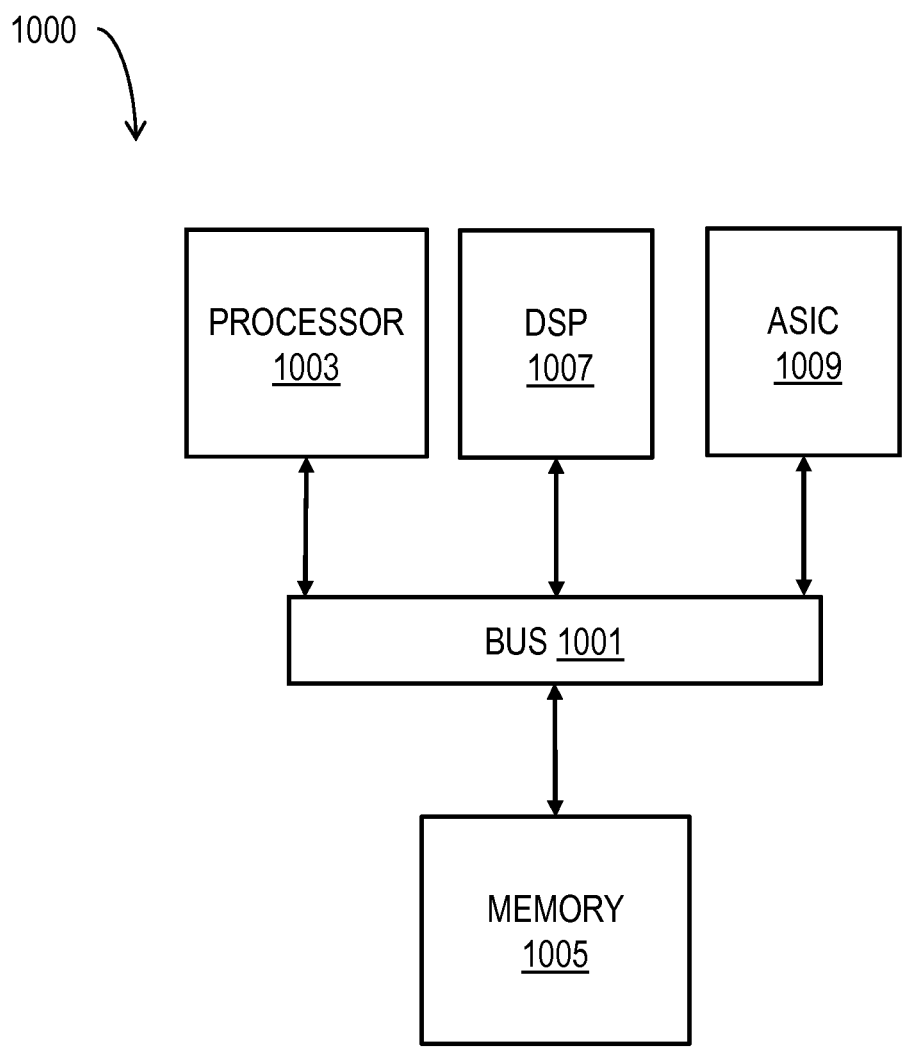
FIG. 10 is a block diagram that illustrates a chip set upon which an embodiment of the invention may be implemented.

FIG. 10 illustrates a chip set 1000 upon which an embodiment of the invention may be implemented. Chip set 1000 is programmed to perform one or more steps of a method described herein and includes, for instance, the processor and memory components described with respect to FIG. 9 incorporated in one or more physical packages (e.g., chips). By way of example, a physical package includes an arrangement of one or more materials, components, and/or wires on a structural assembly (e.g., a baseboard) to provide one or more characteristics such as physical strength, conservation of size, and/or limitation of electrical interaction. It is contemplated that in certain embodiments the chip set can be implemented in a single chip. Chip set 1000, or a portion thereof, constitutes a means for performing one or more steps of a method described herein.

In one embodiment, the chip set 1000 includes a communication mechanism such as a bus 1001 for passing information among the components of the chip set 1000. A processor 1003 has connectivity to the bus 1001 to execute instructions and process information stored in, for example, a memory 1005. The processor 1003 may include one or more processing cores with each core configured to perform independently. A multi-core processor enables multiprocessing within a single physical package. Examples of a multi-core processor include two, four, eight, or greater numbers of processing cores. Alternatively or in addition, the processor 1003 may include one or more microprocessors configured in tandem via the bus 1001 to enable independent execution of instructions, pipelining, and multithreading. The processor 1003 may also be accompanied with one or more specialized components to perform certain processing functions and tasks such as one or more digital signal processors (DSP) 1007, or one or more application-specific integrated circuits (ASIC) 1009. A DSP 1007 typically is configured to process real-world signals (e.g., sound) in real time independently of the processor 1003. Similarly, an ASIC 1009 can be configured to performed specialized functions not easily performed by a general purposed processor. Other specialized components to aid in performing the inventive functions described herein include one or more field programmable gate arrays (FPGA) (not shown), one or more controllers (not shown), or one or more other special-purpose computer chips.

The processor 1003 and accompanying components have connectivity to the memory 1005 via the bus 1001. The memory 1005 includes both dynamic memory (e.g., RAM, magnetic disk, writable optical disk, etc.) and static memory (e.g., ROM, CD-ROM, etc.) for storing executable instructions that when executed perform one or more steps of a method described herein. The memory 1005 also stores the data associated with or generated by the execution of one or more steps of the methods described herein.

4. EXTENSIONS, MODIFICATIONS AND ALTERNATIVES

In the foregoing specification, the invention has been described with reference to specific embodiments thereof. It will, however, be evident that various modifications and changes may be made thereto without departing from the broader spirit and scope of the invention. The specification and drawings are, accordingly, to be regarded in an illustrative rather than a restrictive sense. Throughout this specification and the claims, unless the context requires otherwise, the word "comprise" and its variations, such as "comprises" and "comprising," will be understood to imply the inclusion of a stated item, element or step or group of items, elements or steps but not the exclusion of any other item, element or step or group of items, elements or steps. Furthermore, the indefinite article "a" or "an" is meant to indicate one or more of the item, element or step modified by the article.

What is claimed is:

1. A method comprising:
   injecting a test bolus of a contrast agent into a subject based on a test injection function and scanning a region of interest to obtain a test bolus scan;
   computing an impulse enhancement function based on the test bolus scan;
   determining a target enhancement function for the region of interest based on the contrast agent;
   determining a plurality of parameters for a functional form for a contrast injection function in a time domain;
   determining for the contrast injection function a constraint comprising at least a total volume of contrast agent;
   determining an enhancement function based on the impulse enhancement function and the contrast injection function; and
   determining particular values for the plurality of parameters, which particular values satisfy the constraint and minimize a difference between a value of the enhancement function and the target enhancement function, wherein the difference is computed in the time domain at discrete time periods without use of a Fourier transform; and
   injecting the contrast agent into the subject based on the contrast injection function using the particular values for the plurality of parameters.

2. The method of claim 1, wherein the difference between the enhancement function and the target enhancement function is minimized using a mixed integer solution and wherein at least one parameter is based on an integer variable.

3. The method of claim 2, wherein the at least one parameter based on the integer variable is a time for a change in a rate of injection at each discrete time period, wherein the integer variable is a binary integer variable selected from the domain {0, 1}, and the constraint includes a sum of the times for changes in the rate of injection.

4. The method of claim 3, wherein the constraint on the sum of the times for the changes in the rate of injection is in a range from 2 to 6.

5. The method of claim 1, wherein at least one parameter is a maximum change in a rate of injection.

6. The method of claim 5, wherein the maximum change in the rate of injection is approximately 5 milliliters per second.

7. The method of claim 2, wherein the at least one parameter based on the integer variable is a switch for a rate of injection at each discrete time period, and the integer variable is a binary integer variable selected from the domain {0, 1}.

8. The method of claim 7, wherein the value of the rate of injection at each discrete time period is given by a product of the switch parameter and a value within a range between a minimum value and a maximum value.

9. The method of claim 8, wherein the minimum value is approximately 1.5 milliliters per second and the maximum value is approximately 5 milliliters per second.

10. The method of claim 1, wherein the total volume of contrast agent is based on a sum of a rate of injection of the contrast injection function over all discrete time periods.

11. The method of claim 10, wherein the total volume of contrast agent is in a range from 65 milliliters to 130 milliliters.

12. The method of claim 1, wherein the constraint includes that the contrast injection function is greater than or equal to zero over all discrete time periods.

13. The method of claim 1, wherein the difference is minimized in the time domain over a duration of a plateau of the target enhancement function, wherein the duration of the plateau region is in a range of 5-25 seconds.

14. The method of claim 1, wherein the determining step comprises a stop condition comprising at least one of:
a maximum computation time to minimize the difference between the value of the enhancement function and the target enhancement function in the time domain at discrete time periods; and
a maximum error tolerance in the difference between the value of the enhancement function and the target enhancement function.

15. The method of claim 1, further comprising:
determining a time delay based on an initial time period of the test bolus scan when an average value of the test bolus scan is less than a threshold value; and
scanning the region of interest after injecting the contrast agent based on the contrast injection function and waiting the time delay.

16. The method of claim 1, wherein the difference between the value of the enhancement function and the target enhancement function is expressed as:

$$\sum_{t \in [z(t), z(t)+T]} |h(t) * i(t) - E_l|$$

wherein h(t) is the impulse enhancement function, i(t) is the contrast injection function, h(t)*i(t) is the enhancement function, E1 is the target enhancement function over the time domain, z(t) is the discrete time periods which extend a duration of T in the time domain, and * indicates the convolution operation.

17. The method of claim 16, wherein one of the constraints is a maximum number of changes in a rate of injection over all discrete time periods that is expressed as:

$$\Sigma_t x(t) = A$$

wherein x(t) is a binary integer that is 0 at those discrete time periods when there is no change in the rate of injection and is 1 at those discrete time periods when there is a change in the rate of injection, and wherein A is the maximum number of changes in the rate of injection over all discrete time periods.

18. The method of claim 17, wherein the maximum number of changes is in a range from 2 to 6.

19. The method of claim 16, wherein one of the constraints is an extent of a change in a rate of injection between consecutive discrete time periods that can be expressed as:

$$0 \leq i(t) - i(t+B) \leq Cx(t)$$

wherein B is the discrete time period, C is a maximum extent of change between consecutive discrete time periods and x(t) is a binary integer that is 0 when there is no change in the rate of injection between consecutive discrete time periods and is 1 when there is a reduction in the rate of injection up to C.

20. The method of claim 19, wherein B is approximately 0.1 seconds and C is approximately 5 milliliters per second.

21. The method of claim 16, wherein one of the constraints is a value of a rate of injection at each discrete time period that can be expressed as:

$$Dy(t) \leq i(t) \leq Ey(t)$$

wherein D and E are respective minimum and maximum values of the rate of injection at each discrete time period, and wherein y(t) is a binary integer that is 0 when the value of the rate of injection at each discrete time period is 0 and is 1 when the value of the rate of injection at each discrete time period is within a range between D and E.

22. The method of claim 21, wherein D is approximately 1.5 milliliters per second and E is approximately 5 milliliters per second.

23. The method of claim 1, wherein computing the impulse enhancement function comprises performing a Fourier transform of a test injection function of the test bolus and performing a Fourier transform of the test enhancement function.

24. The method of claim 1, wherein determining the target enhancement function comprises:
measuring a simulated enhancement function based on a simulated bolus scan;
determining a highest level of the simulated enhancement function over a minimum time period; and
equating the target enhancement function in the time domain with the highest level of the simulated enhancement function.

25. The method of claim 24, wherein the minimum time period is in range of 8-10 seconds.

26. The method of claim 1, wherein the contrast injection function comprises a plurality of phases where each phase has a constant rate of injection.

27. The method of claim 1, wherein the test bolus scan is obtained by fitting a skew normal curve to a plurality of sample points to preserve a peak enhancement level of the plurality of sample points.

28. An apparatus comprising:
an injector pump to deliver contrast agent to a subject; and
a processor to transmit a contrast injection function to the injector pump to cause the injector pump to deliver the contrast agent based on the contrast injection function;
wherein the processor is configured to determine the contrast injection function such that a difference between an enhancement function of the contrast injection function and a target enhancement function is minimized over a time domain at discrete time periods without determining a Fourier transform.

29. The apparatus of claim 28, further comprising a scanner to detect images of a region of interest of the subject after delivery of the contrast agent, wherein said processor is configured to determine the enhancement function based on image data received from the scanner.

* * * * *